United States Patent
Tsai et al.

(10) Patent No.: US 9,527,922 B2
(45) Date of Patent: *Dec. 27, 2016

(54) HUMANIZED ALPHA-ENOLASE SPECIFIC ANTIBODIES AND METHODS OF USES IN CANCER THERAPY

(71) Applicants: Development Center for Biotechnology, New Taipei (TW); DCB-USA LLC, Wilmington, New Castle, DE (US); National Health Research Institutes, Miaoli County (TW)

(72) Inventors: Shih-Chong Tsai, New Taipei (TW); Ta-Tung Yuan, New Taipei (TW); Shih-Chi Tseng, New Taipei (TW); Jiann-Shiun Lai, New Taipei (TW); Chia-Cheng Wu, New Taipei (TW); Chao-Yang Huang, New Taipei (TW); Ya-Wei Tsai, New Taipei (TW); Ying-Yung Lok, New Taipei (TW); Chung-Hsiun Wu, New Taipei (TW); Neng-Yao Shih, Miaoli County (TW); Ko-Jiunn Liu, Miaoli County (TW); Li-Tzong Chen, Miaoli County (TW)

(73) Assignees: Development Center for Biotechnology, New Taipei (TW); DCB-USA LLC, Wilmington, New Castle, DE (US); National Health Research Institutes, Miaoli County (TW)

(*) Notice: Subject to any disclaimer, the term of this patent is extended or adjusted under 35 U.S.C. 154(b) by 0 days.

This patent is subject to a terminal disclaimer.

(21) Appl. No.: 14/588,212

(22) Filed: Dec. 31, 2014

(65) Prior Publication Data
US 2016/0185876 A1 Jun. 30, 2016

(51) Int. Cl.
*A61K 39/395* (2006.01)
*C07K 16/40* (2006.01)
*A61K 39/00* (2006.01)

(52) U.S. Cl.
CPC ......... *C07K 16/40* (2013.01); *A61K 2039/505* (2013.01); *C07K 2317/24* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2012/0195900 A1    8/2012   Ghayur et al.

FOREIGN PATENT DOCUMENTS

| GB | 2429013 A | 2/2007 |
|---|---|---|
| WO | 2007/024746 A1 | 3/2007 |
| WO | 2009/114748 A1 | 9/2009 |
| WO | 2011/041894 A1 | 4/2011 |
| WO | 2011/143307 A1 | 11/2011 |
| WO | 2012/175691 A1 | 12/2012 |

OTHER PUBLICATIONS

PCT International Search Report and Written Opinion mailed Apr. 20, 2015, in related International Application No. PCT/US2014/073013 (9 pages).

Primary Examiner — Sheela J Huff
(74) Attorney, Agent, or Firm — Osha Liang LLP

(57) ABSTRACT

A humanized antibody, or a binding fragment thereof, wherein the humanized antibody binds human ENO1 (GenBank: AAH50642.1), wherein the antibody comprises a light chain variable region (VL) domain comprising a CDR1 having the amino acid sequence LCDR1 (RASENIYSYLT; SEQ ID NO: 6) and a CDR2 having the amino acid sequence LCDR2 (NAKTLPE; SEQ ID NO: 7) and a CDR3 having the amino acid sequence LCDR3 (QHHYGTPYT; SEQ ID NO: 8) and an antibody heavy chain variable region (VH) domain comprising a CDR1 having the amino acid sequence HCDR1 (GYTFTSCVMN; SEQ ID NO: 3), a CDR2 having the amino acid sequence HCDR2 (YINPYNDGTKYNEKFKG; SEQ ID NO: 4) and a CDR3 having the amino acid sequence HCDR3 (EGFYYGNFDN; SEQ ID NO: 5), wherein framework regions in the light chain variable region (VL) domain and the heavy chain variable region (VH) domain comprise amino acid sequences from a human immunoglobulin.

15 Claims, 26 Drawing Sheets

FIG.5A

```
Kabat  1    5    10   15   20   25            36   40
       EVQLQQSGPELVKPGASVKMSCKASGYTFTSCVMNWVKQKPGQG    SEQ ID NO:1
                    FR1                 HCDR1        FR2
                                      SEQ ID NO:3

Kabat  45                              66   70   75   80 82ABC
       LEWIGYINPYNDGTKYNEKFKGKATLTSDKSSTAYMELSSLTS    SEQ ID:NO1
              HCDR2                        FR3
              SEQ ID NO:4

Kabat  85   90  9394              105  110
       EDSAVYYCAREGFYYGNFDNWGQGTTLTVSS    SEQ ID:NO1
              HCDR3              FR4
              SEQ ID NO:5
```

FIG.5B

Kabat  1    5    10   15   20                    35   40
DIQMTQSPASLSASVGETVTITCRASENIYSYLTWYQQKQGKS SEQ ID NO:2
                  FR1              LCDR1         FR2
                                   SEQ NO:6

Kabat  45                60    65   70   75   80   85
PQLLVYNAKTLPEGVPSRFSGSGSGTQFSLKINSLQPEDFGSY  SEQ ID NO:2
       LCDR2                   FR3
       SEQ ID NO:7

Kabat                      100  104
YCQHHYGTPYTFGGGTKLEITR          SEQ ID: NO2
   LCDR3        FR4
   SEQ ID NO:8

FIG.6A

Primary alignment of V_L segments

```
              1       5        10       15       20                    LCDR1         35        40
Kabat         DIQMTQSPASLSASVGETVTITC[RASENIYSYLT]WYQQKQGKS
              DIQMTQSPSSLSASVGDRVTITC[RASENIYSYLT]WYQQKPGKA
                              FR1                                                      FR2
                                                                   SEQ ID NO:6

45         LCDR2        60       65       70       75       80       85
Kabat         PQLLVY[NAKTLPE]GVPSRFSGSGSGTQFSLKINSLQPEDFGSY
              PKLLIY[NAKTLPE]GVPSRFSGSGSGTDFTLTISSLQPEDFATY
                                                                              FR3
              SEQ ID NO:7

LCDR3      100    104
Kabat         YC[QHHYGTPYT]FGGGTKLEITR       SEQ ID NO:2
              YC[QHHYGTPYT]FGQGTKLEIKR       SEQ ID NO:9
              SEQ ID NO:8
```

Clone10 : Musmus IGKV12-44*01 F
Human template: V kappa I

FIG.6A (Cont.) Primary alignment of $V_H$ segments

```
Kabat    1       5       10      15      20      25              HCDR1           36    40
         EVQLQQSGPELVKPGASVKMSCKAS [              ] WVKQKPGQG
         EVQLVESGGGLVQPGGSLRLSCAAS [              ] WVRQAPGKG
              FR1                                                        FR2

Kabat        45                              66      70      75      80 82A B C
         LEWIG [                    ] KATLTSDKSSSTAYMELSSLTS
         LEWVA [                    ] RFTISRDDSKNTLYLQMNSLRA
              HCDR2        SEQ ID NO:3                      FR3

Kabat        85   90  93 94                  105     110
         EDSAVYYCAR [               ] WGQGTTLTVSS       SEQ ID NO:1
         EDTAVYYCAR [               ] WGQGTLVTVSS       SEQ ID NO:10
                       SEQ ID NO:4
                          HCDR3
                             SEQ ID NO:5
```

Clone10 = Musmus IGHV1-14*01 F
Human template: VH III

FIG.6B

Primary alignment of V_L segments

```
            1       5        10       15       20          LCDR1        35        40
Kabat       |       |        |        |        |            |           |         |
            DIQMTQSPASLSASVGETVTITC[RASENIYSYLT]WYQQKQGKS
            DIQMTQSPSSLSASVGDRVTITC[RASENIYSYLT]WYQQKPGKA
                      FR1                                                   FR2
                                                          SEQ ID NO:6

45                        60       65       70       75       80       85
Kabat       |                         |        |        |        |        |        |
                LCDR2                                                      FR3
            PQLLVY[NAKTLPE]GVPSRFSGSGSGTQFSLKINSLQPEDFGSY
            PKLLIY[NAKTLPE]GVPSRFSGSGSGTDFTLTISSLQPEDFATY
                          SEQ ID NO:7

100    104
Kabat                     |      |
               LCDR3
            YC[QHHYGTPYT]FGGGTKLEITR          SEQ ID NO:2
            YC[QHHYGTPYT]FGQGTKLEIKR          SEQ ID NO:9
               SEQ ID NO:8
```

Clone10 : Musmus IGKV12-44*01 F
Human template: V kappa I

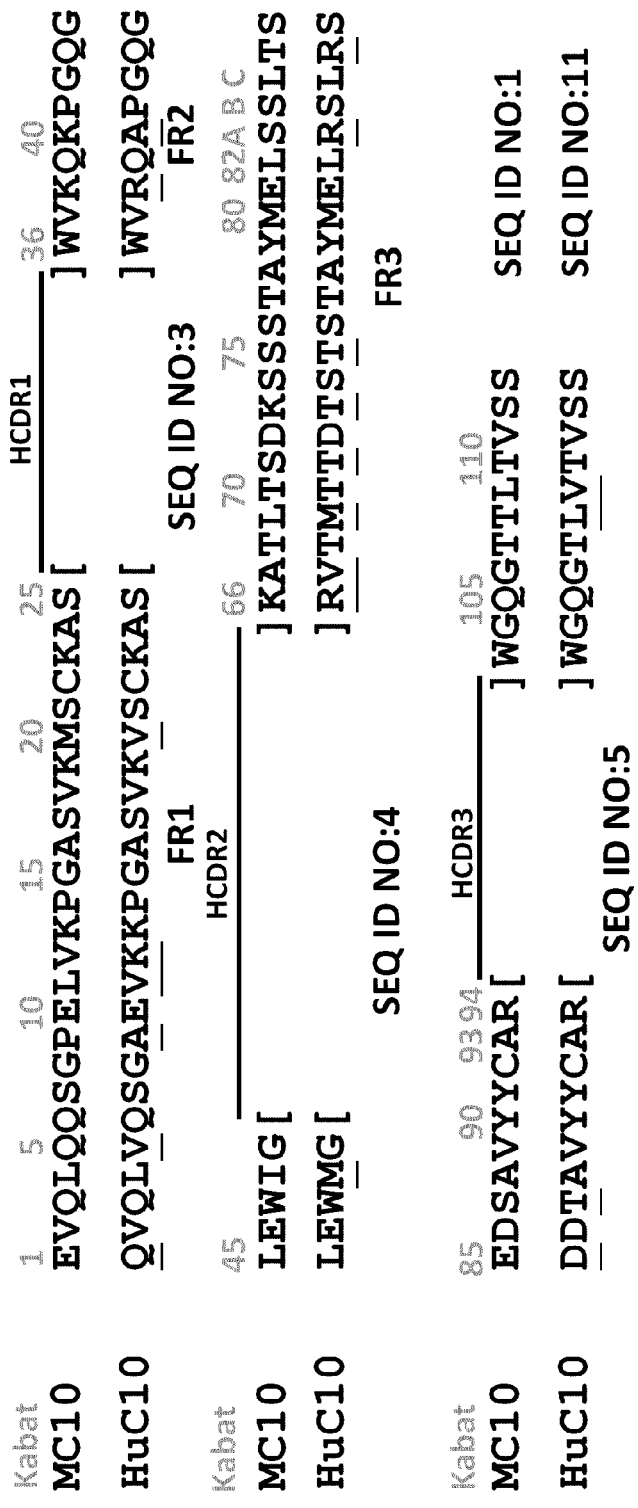

FIG.6B (Cont.) Primary alignment of V_H segments

```
Kabat    1       5        10        15        20        25              HCDR1      36        40
MC10     EVQLQQSGPELVKPGASVKMSCKAS [                    ] WVKQKPGQG
HuC10    QVQLVQSGAEVKKPGASVKVSCKAS [                    ] WVRQAPGQG
                        FR1                                                                    FR2
                                                        HCDR2
                                                     SEQ ID NO:3

Kabat   45                    66       70       75       80 82A B C
MC10    LEWIG [                      ] KATLTSDKSSSTAYMELSSLTS
HuC10   LEWMG [                      ] RVTMTTDTSTSTAYMELRSLRS
                                                                   FR3
                  SEQ ID NO:4

Kabat   85     90  93 94         HCDR3      105      110
MC10    EDSAVYYCAR [                  ] WGQGTTLTVSS           SEQ ID NO:1
HuC10   DDTAVYYCAR [                  ] WGQGTLVTVSS           SEQ ID NO:11
                   SEQ ID NO:5
```

Clone10: Musmus IGHV1-14*01 F
Human template (database): IGHV1-18*01 F/IGHJ4*03

Table II: The binding Kinetics of EN10 antibodies by SPR

| Antibody names | ENO1 | | | | | Capture Level |
|---|---|---|---|---|---|---|
| | Ka | Kd | KD | Rmax(RU) | Chi$^2$(RU$^2$) | |
| Chimera EN10 mAb | 3.577E+5 | 8.271E-5 | 2.313E-10 | 176.8 | 0.668 | 325 |
| Hum EN10 mAb IMGT | 5.311E+5 | 1.162E-4 | 2.188E-10 | 140.0 | 0.656 | 290 |
| Chimera EN10 mAb | 3.575E+5 | 8.250E-5 | 2.308E-10 | 123.1 | 1.10 | 380 |
| Hum EN10 mAb 4D5 | 3.511E+5 | 1.755E-4 | 4.997E-10 | 100.3 | 0.361 | 355 |

FIG.13A

```
          10        20        30        40        50        60
GACATCCAGATGACCCAGTCCCCCTCCCAGCCTGTCTGCCTCTGTGGGCGACAGAGTGACC
:: ::::::::::::::: ::      ::::::::  : :::::::: :::::: :::::
GATATCCAGATGACCCAGTCCCCCAGCTCCCTGTCCGCCTCTGTGGGCGATAGGGTCACC 70        80        90       100       110       120
ATCACCTGTGCGGCCTCCGAGAACATCTACTCCTACCTGACCTGGTATCAGCAGAAGCCC
:: :::::::   :: ::::: :::::::: :::  :::: :: :::: ::::::: :::
ATCACCTGTGCCAGCCTGGAGCAAGTGAGAATATTTACAGTTATTTAACATGGTATCAACAGAAACCA 130       140       150       160       170       180
GGCAAGGCCCCCAAGCTGCTGATCTACAAGCCAAGACCCTGCCCGAGGGCGTGCCCTCT
::::::::   ::::::: ::::::: :: :: ::    ::: :: ::::: ::: ::
GGAAAAGCTCCGAAACTACTGATTTACAATGCAAAAACCTTACCAGAAGGAGTCCCTTCT 190       200       210       220       230       240
AGATTCTCCGGCTCTGGCTCTGGCACCGACTTTACCCTGACCATCAGCTCCCTGCAGCCC
: ::::::::::: :  : ::::::::: :: ::: :::: ::::::: :::::::: :
CGCTTCTCTGGTTCCGGCTCTGGAGACGAATTCACTCTGACCATCAGCAGTCTGCAGCCG 250       260       270       280       290       300
GAGGACTTCGCCACCTACTACTGCCAGCACCACTACGGCACCCCTACACCTTTGGCCAG
::::::::::: ::::::::::::::::::::  ::: ::     ::: ::  :::::
GAAGACTTCGCAACCTATTACTGTCAACATCATTATGGTACTCCGTACACGTTCGGACAG 310       320
GGCACCAAGGTGGAAATCAAGCGG        SEQ ID NO:14
:: ::::::::::::: ::::: :
GGTACCAAGGTGGAGATCAAACG         SEQ ID NO:15
```

| 14D Rank | Clone ID | EN10.3 Day 14 Titer (mg/L) | Day 5 Titer (mg/L) |
|---|---|---|---|
| 1 | FF6D5 | 358.7 | 155 |
| 2 | FF5H7 | 349.4 | 147 |
| 3 | FF6C6 | 331.1 | 125.2 |
| 4 | FF7D10 | 319.8 | 118.9 |
| 5 | FF8G7 | 318.8 | 131.9 |
| 6 | FF4B7 | 302.4 | 153.6 |
| 7 | FF5F12 | 302 | 135 |
| 8 | FF3D2 | 284.4 | 119.2 |
| 9 | FF5F11 | 282.8 | 134.6 |
| 10 | FF6F5 | 277.6 | 154 |
| 11 | FF4C7 | 267.1 | 94.2 |
| 12 | FF1D9 | 259.8 | 90.4 |
| 13 | FF6F9 | 255.7 | 125.3 |
| 14 | FF2D5 | 255.3 | 124.6 |
| 15 | FF5F10 | 247.5 | 91.3 |

HUMANIZED ALPHA-ENOLASE SPECIFIC ANTIBODIES AND METHODS OF USES IN CANCER THERAPY

FIELD OF THE INVENTION

The present invention relates to methods for generation of humanized antibodies that bind specifically to the human alpha-enolase protein (ENO1). The present invention also relates to methods for developing humanized anti-alpha-enolase antibody producing cell line and methods for suppressing tumor growth and metastasis using an humanized antibody to bind alpha-enolase proteins (ENO1) in cancer cells.

BACKGROUND OF THE INVENTION

Tumors result from aberrant, unrestrained proliferation of a single cell, generating a clone of transformed cells. Cancer is characterized by tumor cells' autonomous growth and ability to metastasize to distant sites.

Tumor cells may express unique antigens that can be recognized by the immune system. Tumor-associated antigens include, but are not limited to, mutated oncogenes, mutated normal cellular proteins, aberrantly expressed cellular proteins, abnormal cell-surface proteins, and oncogenic viral proteins. The immune system views these tumor-associated antigens as non-self and can produce antibodies to eradicate these foreign antigen-bearing tumor cells, while sparing the healthy cells. Therefore, identification of immunogenic tumor-associated antigens may be used as targets for clinical prognostic or therapeutic applications in cancer treatment.

Certain malignancies may be identified by pleural effusion, which is excess fluid in the space between the lung and chest wall. Lung carcinoma, breast carcinoma, and lymphoma cause about 75% of all malignant pleural effusions. Malignant pleural effusion may be enriched with lymphocytic infiltrates and tumor cells. Tumor-associated immune complexes or autoantibodies, such as anti-p53, antinuclear, and anti-=c-Myc antibodies, have been found in effusion fluids and are associated with poor prognosis. Several lung tumor-associated antigens have also been identified in malignant effusion, including, cytokeratin 19 fragments, neuron-specific enolase (ENO2), squamous cell carcinoma antigen, and soluble HLA-I, etc.

Alpha-enolase (enolase-1, ENO1) is a multiple functional protein, which was first found as a key enzyme of the glycolysis pathways. Under normal conditions, ENOL is expressed in the cytosol. However, ENO1 is also found to express on the cell surfaces of many cancer cells as a plasminogen receptor and on activated hematopoietic cells, such as neutrophils, lymphocytes and monocytes. It is known that the up-regulation of plasminogen receptor proteins can induce a cascade response of the urokinase plasmongen activation system (uPAS).

The urokinase plasminogen activator system (uPAS) consists of the urokinase plasminogen activator (uPA), its cognate receptor (uPAR) and two specific inhibitors, the plasminogen activator inhibitor 1 (PAI-1) and plasminogen activator inhibitor 2 (PAI-2). Urokinase plasminogen activator converts plasminogen proenzyme into an active serine protease, plasmin. Plasmin is involved in a number of tissue remodeling processes, such as basement membrane (BM) and extracellular matrix (ECM) remodeling, which is required in tumor progression and metastasis. In addition, it has been shown that the uPAS may be involved in the neoplastic evolution, affecting tumor angiogenesis, malignant cell proliferation, adhesion and migration, intra-vascularization, and growth at the metastatic site.

Specifically, activation of plasminogen can result in extracellular matrix degradations, which in turn can lead to increased metastasis of cancer cells and infiltration of immune cells. In other words, ENO1 expression on cancer cell surfaces as a plasminogen receptor can increase invasion activities of the cancer cells. Therefore, ENO1 is a potential target for cancer therapy.

SUMMARY OF THE INVENTION

Embodiments of the invention relate to targeted binding agents (e.g., antibodies, or binding fragments thereof) that specifically bind human ENO1, thereby inhibiting ligand (e.g., plasminogen) binding to ENO1. By inhibiting binding of plasminogen to ENO1, targeted binding agents of the invention can inhibit plasminogen activation, leading to reduced degradation of extracellular matrix, which in turn prevents or reduces dissociation of cancer cells from the extracellular matrix. Therefore, targeted binding agents in accordance with embodiments of the invention can be used to inhibit tumor growth and metastasis. Mechanisms by which this can be achieved may include, but are not limited to, inhibition of binding of a ligand (such as plasminogen) to its receptor ENO1, or abrogation of inter-reactions between the receptor ENO1 and its ligands, thereby reducing the effective concentration of ENO1.

In accordance with one embodiment of the invention, a targeted binding agent is a humanized antibody that can bind to human ENO1 to prevent its ligands (e.g., plasminogen) from binding to ENO1. Preventing binding of plasminogen to the receptor can prevent plasminogen activation. This results in the inhibition of the urokinase plasminogen activation system (uPAS) in the extracellular matrix of cancer cells.

In accordance with some embodiments of the invention, the humanized antibody may bind ENO1 with high affinities, such as with a $K_d$ of less than 0.3 nM. Such tight binding agents can inhibit ENO1 with high efficiencies.

In accordance with some embodiments of the invention, a targeted binding agent is an humanized antibody that can bind to human ENO1 and inhibit induced plasmin activity on cancer cells with high efficiencies, such as 40%, 50%, 60%, 70%, 80%, 90%, or 100% inhibition. The inhibition assays may be performed by inducing ENO1 expression (hence, plasminogen activation) in a cancer cell (such as U937 human lymphoma cells) by treatment with an inducer, such as lipopolysaccharide (LPS) (e.g., 10 microgram/mL, for 5 hours). Inhibition of such induced plasmin activity may be assayed with an antibody at a suitable concentration. Using an antibody of the invention, such inhibition may be detected at antibody concentrations as low as 20 microgram/ml or less.

In accordance with some embodiments of the invention, a targeted binding agent is an antibody that can bind to human ENO1. Such an antibody may be used to inhibit the invasion activity of a cancer cell. For example, antibodies of the invention can inhibit greater than 40%, 50%, 60%, or 70% of the invasion activity of U937 human lymphoma cells at antibody concentrations as low as 50 microgram/ml or less.

In accordance with some embodiments of the invention, a targeted binding agent is an antibody that can bind to human ENO1 to inhibit extracellular matrix degradation, thereby inhibiting cancer cell dissociation from the extracellular matrix. For example, an antibody of the invention can inhibit greater than 40%, 50%, or 60% of plasminogen mediated dissociation of CL1-5 cells from collagen or fibronectin at antibody concentrations as low as 50 microgram/ml or less.

In accordance with embodiments of the invention, a targeted binding agent (i.e. a humanized antibody) may comprise a heavy chain variable region amino acid sequence of SEQ ID NO: 1, 10 or 11.

In accordance with embodiments of the invention, a targeted binding agent (i.e. a humanized antibody) may comprise a light chain variable region amino acid sequence of SEQ ID NO: 2 or 9.

In accordance with embodiments of the invention, a targeted binding agent (i.e. an antibody) may comprise a heavy chain amino acid sequence having a complementarity determining region (CDR) comprising one of the CDR sequences included in sequences 1, 10 or 11. It is noted that those of ordinary skill in the art can readily accomplish CDR determinations. See for example, Kabat et al., "*Sequences of Proteins of Immunological Interest*," Fifth Edition, NIH Publication 91-3242, Bethesda Md. (1991), vols. 1-3.

In accordance with some embodiments of the invention, a targeted binding agent (i.e. an antibody) may comprise a light chain amino acid sequence having a complementarity determining region (CDR) comprising one of the CDR sequences included in sequence 2 or 9 (FIG. 6B).

In accordance with some embodiments of the invention, a targeted binding agent is a humanized antibody, or a binding fragment thereof, wherein the antibody may be a monoclonal antibody.

In accordance with some embodiments of the invention, a humanized antibody that can bind human ENO1 protein comprises a light chain amino acid sequence comprising any one of LCDR1, LCDR2 or LCDR3 sequences included in SEQ ID NO: 9 (FIG. 6B).

In accordance with some embodiments of the invention, a humanized antibody that can bind human ENO1 protein comprises a light chain amino acid sequence comprising any two of LCDR1, LCDR2 or LCDR3 sequence included in sequence 2 or 9 (that is, LCDR1 and LCDR2, LCDR1 and LCDR3 or LCDR2 and LCDR3).

In accordance with some embodiments of the invention, a humanized antibody that can bind human ENO1 protein comprises a light chain amino acid sequences that comprises LCDR1, LCDR2 and LCDR3 sequences included in sequence 2 or 9 (FIG. 6B). In accordance with certain embodiments of the invention, an antibody may be a humanized antibody or a fully human monoclonal antibody.

In accordance with some embodiments of the invention, an humanized antibody that can bind human ENO1 protein comprises a heavy chain amino acid sequence comprising any one of HCDR1, HCDR2 or HCDR3 sequence included in sequence 1, 10, or 11 (FIG. 6A and FIG. 6B).

In accordance with some embodiments of the invention, a humanized antibody that can bind human ENO1 protein comprises a heavy chain amino acid sequence that comprises any two of HCDR1, HCDR2 or HCDR3 sequence included in n sequence 1, 10, or 11 (FIG. 6A and FIG. 6B). (that is, HCDR1 and HCDR2, HCDR1 and HCDR3 or HCDR2 and HCDR3).

In accordance with some embodiments of the invention, a humanized antibody that can bind human ENO1 protein comprises a heavy chain amino acid sequence that comprises HCDR1, HCDR2 and HCDR3 sequences included in sequence 1, 10 or 11 (FIG. 6A and FIG. 6B).

In accordance with some embodiments of the invention, a humanized antibody that can bind human ENO1 protein comprises a light chain amino acid sequence having a CDR comprising one of the CDR sequences included in sequence 2 or 9 (FIG. 6B). In accordance with some embodiments of the invention, a humanized antibody can bind human ENO1 protein and comprises a heavy chain amino acid sequence having a CDR comprising one of the sequences shown in sequence 1, 10, or 11. In accordance with some embodiments of the invention, a humanized antibody that can bind human ENO1 protein comprises a heavy chain amino acid sequence having one of the CDR sequences included in sequence 1, 10, or 11, and a light chain amino acid sequence having one of the CDR sequences included in sequence 2 or 9.

In accordance with some embodiments of the invention, a targeted binding agent (i.e. an antibody) can compete for binding of plasminogen to human ENO1 protein. In accordance with some embodiments of the invention, said targeted binding agent comprises a heavy chain amino acid sequence having at least one of the CDR sequences included in sequence 1, 10, or 11, and a light chain amino acid sequence having at least one of the CDR sequences included in sequence 2 or 9.

Some embodiments of the invention relate to methods for assaying the level of human ENO1 protein in a patient or a patient sample. A method of the invention comprises contacting a humanized anti-ENO1 antibody with a biological sample from a patient, and detecting the level of binding between said antibody and human ENO1 protein in said sample. In more specific embodiments, the biological sample is blood or plasma.

Other embodiments of the invention relate to compositions comprising a targeted binding agent, which may include a humanized antibody or a functional fragment thereof, and a pharmaceutically acceptable carrier.

Still further embodiments of the invention relate to methods for effectively treating a subject (e.g., human or animal) suffering from an ENO1 disease or disorder. The method may include selecting a subject in need of a treatment for a neoplastic or non-neoplastic disease, and administering to the subject a therapeutically effective dose of an antibody (which may be a humanized or a fully human monoclonal antibody) that specifically binds to ENO1 protein.

The humanized antibody of the invention can be used to treat a human ENO1 protein-related disease or disorder. A human ENO1 protein related disease or disorder may be any condition arising from aberrant activation or expression of human ENO1 protein. Examples of such diseases include where human ENO1 protein aberrantly interacts with its ligands, thereby altering cell-adhesion or cell signaling properties. This alteration in cell adhesion or cell signaling properties can result in neoplastic diseases or some immune diseases.

For example, a human ENO1 protein-related disease may be a neoplastic disease, such as lung, breast, pancreas, liver, colorectal, and prostate cancers.

Additional embodiments of the invention relate to methods for inhibiting ENO1-induced cell dissociation from extracellular matrix of cancers in a subject. These methods may include selecting a subject (e.g., a human or an animal) in need of treatment for ENO1-induced cell dissociation, and administering to said subject a therapeutically effective dose of an antibody, wherein said antibody specifically binds to ENO1. The antibody is a humanized or fully human monoclonal antibody.

Further embodiments of the invention relate to the uses of a humanized antibody in the preparation of a medicament for the treatment of an ENO1-related disease or disorder in a subject (e.g., a human or an animal), wherein said antibody specifically binds to ENO1. The antibody is a humanized or fully human monoclonal antibody.

In accordance with some embodiments of the invention, the targeted binding agents described herein can be used for the preparation of a medicament for the treatment of ENO1 protein-induced cell dissociation from extracellular matrix in an animal, wherein said antibody specifically binds to ENO1. The antibody is a humanized or fully human monoclonal antibody.

Some embodiments of the invention described herein relate to monoclonal antibodies that bind human ENO1 and affect human ENO1 functions. Other embodiments of the invention relate to anti ENO1 antibody preparations with desirable properties for therapy applications. Such properties may include a high binding affinity for ENO1, the ability to neutralize ENO1 activity in vitro and in vivo, and the ability to inhibit ENO1 induced cell dissociation, growth and metastasis of tumors.

In some embodiments, the invention relates to a humanized antibody that can bind to human ENO1 with very high affinity (i.e., low $K_d$). For example a humanized antibody that is capable of binding ENO1 with a $K_d$ less than about $10^{-5}$, $10^{-6}$, $10^{-7}$, $10^{-8}$, $10^{-9}$, $10^{-10}$ or about $10^{-11}$ M, or any range or value there between. Affinity and/or avidity measurements can be performed using ELISA and/or BIA-CORE, as described herein or according to techniques known in the art.

It will be appreciated that embodiments of the invention are not limited to any particular form of an antibody or method of generation or production. For example, the anti-ENO1 antibody may be a full-length antibody (e.g., having an intact human Fc region) or an antibody fragment (e.g., a Fab, Fab' or F(ab')$_2$, FV or Dab (Dabs are the smallest functional binding units of human antibodies). In addition, the antibody may be manufactured from a recombinantly produced cell that has been transformed or transfected with a gene or genes encoding the humanized antibody.

Other embodiments of the invention relate to isolated nucleic acid molecules encoding any of the humanized antibodies described herein, vectors having isolated nucleic acid molecules encoding a humanized anti-ENO1 antibody or a host cell transformed with any of such nucleic acid molecules.

In addition, some embodiments of the invention relate to a method for producing a humanized anti-ENO1 antibody by culturing host cells under conditions wherein a nucleic acid molecule is expressed to produce the antibody, followed by recovering the antibody. It should be realized that embodiments of the invention may also include any nucleic acid molecule which encodes a humanized antibody or fragment of a humanized antibody of the invention including nucleic acid sequences optimized for increasing yields of antibodies or fragments thereof when transfected into host cells for antibody production.

Other embodiments relate to the generation and identification of isolated humanized antibodies that can bind specifically to human ENO1. Inhibition of the biological activity of ENO1 can be effected by these antibodies to prevent ENO1 induced cell dissociation, invasion and other desired effects of cancers.

Other embodiments of the invention relate to pharmaceutical compositions having an effective amount of a humanized anti-ENO1 antibody. The composition may further comprise a pharmaceutically acceptable carrier or diluent. In yet other embodiments, the anti-ENO1 antibody, or a fragment thereof, is conjugated to a therapeutic agent. The therapeutic agent can be, for example, a toxin or a radioisotope.

Yet other embodiments of the invention relate to methods for treating diseases or conditions associated with the expression of ENO1 in a patient. The methods may include administering to a patient an effective amount of a humanized anti-ENO1 antibody. The humanized anti-ENO1 antibody can be administered alone, or can be administered in combination with additional antibodies or chemotherapeutic drug or radiation therapy. For example, a monoclonal, oligoclonal or polyclonal mixture of ENO1 antibody that block cell dissociation can be administered in combination with a drug shown to inhibit tumor cell proliferation directly. The method can be performed in vivo and the patient is preferably a human patient. In a preferred embodiment, the method concerns the treatment of an ENO1-related disease or disorder including, but not limited to, neoplastic diseases, such as lung, breast, pancreas, liver, colorectal, prostate cancers and or solid tumors.

Some embodiments of the invention relate to a method for monitoring cancer development. The method may comprise determining the abundance of alpha-enolase proteins (ENO1) in a sample (e.g., cancer cells), wherein an increased level of ENO1 correlates with cancer severity. In accordance with embodiments of the invention, the abundance may be determined by measuring binding of an ENO1 specific antibody to the ENO1 proteins.

Some embodiments of the invention relate to a method for detecting cancer. Such a method may comprise determining the abundance of ENO1-specific antibodies in serum samples, wherein a low level of ENO1-specific antibodies indicates the presence of a malignant tumor.

BRIEF DESCRIPTION OF THE DRAWINGS

FIG. 5A depicts the variable heavy chain region amino acid sequence of EN10 mAb (SEQ ID NO: 1). The framework regions (FR1, FR2, FR3, and FR4) and CDRs (HCDR1, HCDR2, and HCDR3) are indicated. Cloning the EN10 mAb was performed as described in Example 5.

FIG. 5B depicts the variable light chain region amino acid sequence of EN10 mAb (SEQ ID NO: 2). The framework regions (FR1, FR2, FR3, and FR4) and CDRs (LCDR1, LCDR2, and LCDR3) are indicated. Cloning the EN10 mAb was performed as described in Example 5.

FIG. 6A shows the sequence analysis made for humanization of the VL (sequence ID NO:9) and VH (sequences ID NO:10) sequences of hum ENO10 mAb 4D5. In the first line showing with under the residue numbering according the Kabat scheme, the mask is shown with underling, and the Kaba CDRs are shown in under lines. To determine the frame works of VL and VH of humEN10 mAb 4D5 were performed as described in Example 6.

FIG. 6B shows the sequence analysis made for humanization of the VL (sequence ID NO:9) and VH (sequences ID NO:11) sequences of hum ENO10 mAb IMGT. In the first line showing with under the residue numbering according the Kabat scheme, the mask is shown with underling, and the Kaba CDRs are shown in under lines. To determine the frame works of VL and VH of humEN10 mAb IMGT were performed as described in Example 6.

FIG. 13A shows the sequence analysis made for the codon optimization of the VL (sequence ID NO: 9) and VH (sequences ID NO: 10) sequences of humEN10 mAb IMGT expressed in the CHOS cell line. Detailed procedures were performed as described in Example 13.

FIG. 13B depicts an expression vector for the generation of humanized antibody of hum EN10 IMGT in the CHOS stable cell line. Detailed procedures were performed as described in Example 13.

FIG. 13D shows the titers of antibodies from top 15 stable clones, which expressed hum EN10 mAb IMGT antibody. Detail procedures were performed as described in Example 13.

DEFINITIONS

Figure 1:
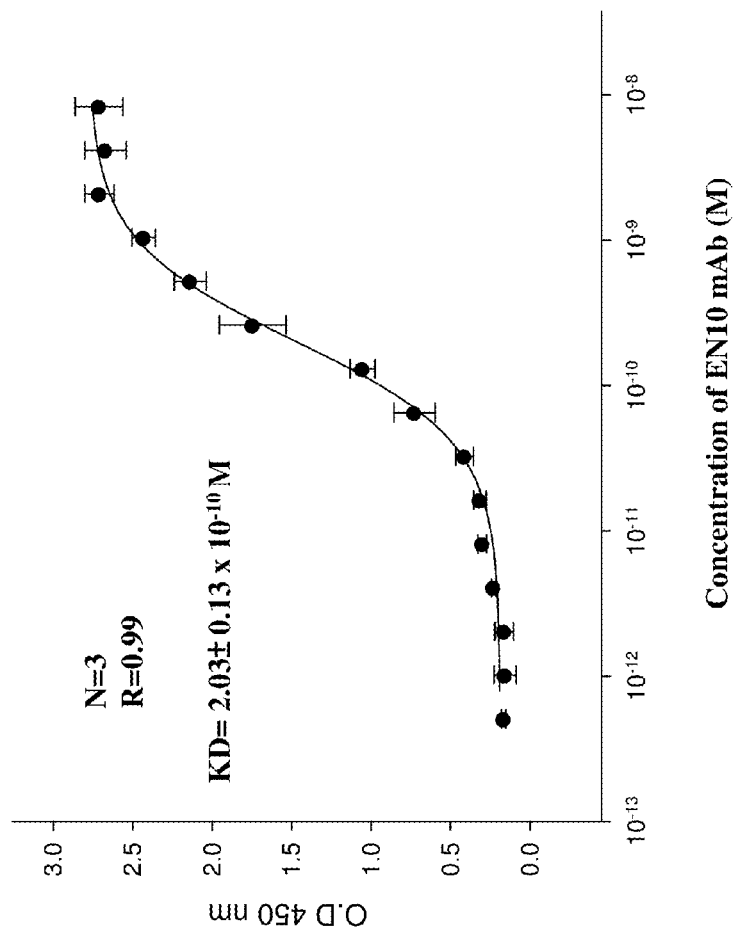
FIG. 1 shows ELISA results from ENO1 binding by EN10 mAb isolated from acites of hybridoma. Ammonium sulfate purification, protein A column purification, and SDS-PAGE purification were performed as described in Example 1. These data show the Kd of anti-human ENO1 antibody EN10 mAb.

Unless otherwise defined, scientific and technical terms used herein shall have the meanings that are commonly understood by those of ordinary skill in the art. Furthermore, unless otherwise required by context, singular terms shall include pluralities and plural terms shall include the singular. Generally, nomenclatures used in connection with, and techniques of, cell and tissue culture, molecular biology, and protein and oligo- or polynucleotide chemistry and hybridization described herein are those well-known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al., Molecular Cloning: A Laboratory Manual (3rd ed., Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings: The term "and/or" as used herein is to be taken as specific disclosure of each of the two specified features or components with or without the other. For example "A and/or B" is to be taken as specific disclosure of each of (i) A, (ii) B and (iii) A and B, just as if each is set out individually herein.

An antagonist may be a polypeptide, nucleic acid, carbohydrate, lipid, small molecular weight compound, an oligonucleotide, an oligopeptide, interference RNA (RNAi), antisense, a recombinant protein, an antibody, or conjugates or fusion proteins thereof. For a review of RNAi, see Milhavet O, Gary D S, Mattson M P. (Pharmacol Rev. 2003 December; 55(4):629-48. Review.) and for antisense approach, see Opalinska J B, Gewirtz A M. (Sci STKE. 2003 Oct. 28; 2003 (206): pe47).

Disease-related aberrant activation or expression of "ENO1" may be any abnormal, undesirable or pathological cell adhesion, for example tumor-related cell adhesion. Cell adhesion-related diseases include, but are not limited to, non-solid tumors such as leukemia, or lymphoma, and also solid tumors such as melanoma, non-small cell lung cancer, hepatocellular (liver) carcinoma, gastric, head and neck, hepatic system, stomach, breast, ovary, lung, lung, uterus, vulva, colorectum, and pancreas.

The term ENO1 refers to the heterodimer enolase molecule consisting of an ENO1 and ENO2 or ENO3.

As used herein, the term "antibody" refers generally and broadly to immunoglobulins, autoantibodies, monoclonal antibodies, and polyclonal antibodies, as well as active fragments thereof. The fragment may be active in that it binds to the cognate antigen, or it may be active in that it is biologically functional. The antibodies of the invention may be chimeric, humanized, or human, using techniques known in the art.

As used herein, the term "monoclonal antibody" refers to antibodies that are chemically and immunologically homogeneous, generally produced by hybridomas. See A Laboratory Manual, Harlow and Lane, eds., Cold Spring Harbor, N.Y. (1988).

As used herein, the term "polyclonal antibody" refers to antibodies that are produced by more than one clone of antibody-synthesizing plasma cells (B-lymphocytes) in response to the same antigen. They are generally produced by the animal after it is immunized with the antigen.

As used herein, the term "chimeric antibody" refers to antibodies that contain sequences from more than one source. For example, such antibodies may contain sequences from non-human sources that are then modified by introducing human sequences.

As used herein, the term "humanized antibody" refers to an antibody in which minimal portions of a non-human antibody are introduced into an otherwise human antibody.

As used herein, the term "human antibody" refers to an antibody in which substantially every part of the protein is substantially non-immunogenic in humans, with only minor sequence changes or variations.

As used herein, the term "alpha-enolase specific antibody" refers to an antibody that has a high specificity for mammalian ENO1, but not to ENO2 or ENO3.

As used herein, the term "ENO1-specific antibody" refers to an antibody that binds the alpha-enolase protein.

The term "neutralizing" when referring to a targeted binding agent, such as an antibody, relates to the ability of said targeted binding agent to eliminate, or significantly reduce, the activity of a target antigen. Accordingly, a "neutralizing" ENO1 antibody is capable of eliminating or significantly reducing the activity of ENO1. A neutralizing ENO1 antibody may, for example, act by blocking the binding of ENO1 to the plasminogen. By blocking this binding, the plasminogen mediated cell dissociation is significantly, or completely, eliminated. Ideally, a neutralizing antibody against ENO1 enhances cell adhesion.

The term "isolated polynucleotide" as used herein shall mean a polynucleotide that has been isolated from its naturally occurring environment. Such polynucleotides may be genomic, cDNA, or synthetic. Isolated polynucleotides preferably are not associated with all or a portion of the polynucleotides they associate with in nature. The isolated polynucleotides may be operably linked to another polynucleotide that it is not linked to in nature. In addition, isolated polynucleotides preferably do not occur in nature as part of a larger sequence.

The term "isolated protein" referred to herein means a protein that has been isolated from its naturally occurring environment. Such proteins may be derived from genomic DNA, cDNA, recombinant DNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa or lambda light chain immunoglobulin molecules, and vice versa, as well as fragments and analogs thereof. Preferred polypeptides in accordance with the invention may also comprise solely the human heavy chain immunoglobulin molecules or fragments thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "polynucleotide" as referred to herein means a polymeric form of nucleotides of at least 10 bases in length, either ribonucleotides or deoxynucleotides or a modified form of either type of nucleotide, or RNA-DNA heteroduplexes. The term includes single and double stranded forms of DNA.

The term "oligonucleotide" referred to herein includes naturally occurring, and modified nucleotides linked together by naturally occurring, and non-naturally occurring linkages. Oligonucleotides are a polynucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoranilaldate, phosphoroamidate, and the like. See e.g., LaPlanche, et al., Nucl. Acids Res. 14:9081 (1986); Stec, et al., J. Am. Chem. Soc. 106:6077 (1984); Stein, et al., Nucl. Acids Res. 16:3209 (1988); Zon, et al., Anti-Cancer Drug Design 6:539 (1991); Zon, et al., Oligonucleotides and Analogues: A Practical Approach, pp. 87-108 (F. Eckstein, Ed., Oxford University Press, Oxford England (1991)); Stec, et al., U.S. Pat. No. 5,151,510; Uhlmann and Peyman Chemical Reviews 90:543 (1990), the disclosures of which are hereby incorporated by reference. An oligonucleotide can include a label for detection, if desired.

The term "CDR region" or "CDR" is intended to indicate the hypervariable regions of the heavy or light chains of the immunoglobulin as defined by Kabat, et al., 1991 (Kabat, E. A. et al., (1991) Sequences of Proteins of Immunological Interest, 5th Edition. US Department of Health and Human Services, Public Service, NIH, Washington), and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It may be as short as 2 amino acids, although the longest size known is 26. CDR length may also vary according to the length that can be accommodated by the particular underlying framework. Functionally, HCDR3 plays a role in part in the determination of the specificity of the antibody (Segal, et al., PNAS, 71:4298-4302, 1974, Amit, et al., Science, 233:747-753, 1986, Chothia, et al., J. Mol. Biol., 196:901-917, 1987, Chothia, et al., Nature, 342:877-883, 1989, Caton, et al., J. Immunol., 144:1965-1968, 1990, Sharon, et al., PNAS, 87:4814-4817, 1990, Sharon, et al., J. Immunol, 144:4863-4869, 1990, Kabat, et al., J. Immunol., 147:1709-1719, 1991).

The term a "set of CDRs" referred to herein comprises CDR1, CDR2 and CDR3. Thus, a set of HCDRs refers to HCDR1, HCDR2 and HCDR3 (LCDR refers to a variable heavy chain CDR), and a set of LCDRs refers to LCDR1, LCDR2 and LCDR3 (LCDR refers to a variable light chain CDR). Unless otherwise stated, a "set of CDRs" includes HCDRs and LCDRs.

Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. It should be appreciated that there can be differing regions of homology within two orthologous sequences. For example, the functional sites of mouse and human orthologues may have a higher degree of homology than non-functional regions.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA."

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity.

The terms "substantial identity" or "substantially identical" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2.sup.nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ϵ-N,N,N-trimethyllysine, ϵ-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least about 75%, more preferably at least 80%, 90%, 95%, and most preferably about 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site.

Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxyl-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie, et al., (1991) Science 253:164. Thus, the foregoing examples demonstrate that those of skill in the art can recognize sequence motifs and structural conformations that may be used to define structural and functional domains in accordance with the antibodies described herein.

A further aspect of the invention is a targeting binding agent or an antibody molecule comprising a VH domain that has at least about 60, 70, 80, 85, 90, 95, 98, or about 99% amino acid sequence identity with a VH domain of any of antibodies shown in sequences 1, the appended sequence listing, an antibody described herein, or with an HCDR (e.g., HCDR1, HCDR2, or HCDR3) shown in sequences 1. The targeting binding agent or antibody molecule may optionally also comprise a VL domain that has at least about 60, 70, 80, 85, 90, 95, 98, or about 99% amino acid sequence identity with a VL domain any of antibodies shown in sequences 2, the appended sequence listing, an antibody described herein, or with an LCDR (e.g., LCDR1, LCDR2, or LCDR3) shown in sequences 2. Algorithms that can be used to calculate % identity of two amino acid sequences comprise e.g. BLAST (Altschul, et al., (1990) J. Mol. Biol. 215: 405-410), FASTA (Pearson and Lipman (1988) PNAS USA 85: 2444-2448), or the Smith-Waterman algorithm (Smith and Waterman (1981) J. Mol. Biol. 147: 195-197), e.g. employing default parameters. In some embodiments, the targeting binding agent or antibody that shares amino acid sequence identity as describes above, exhibits substantially the same activity as the antibodies referenced. For instance, substantially the same activity comprises at least one activity that differed from the activity of the references antibodies by no more that about 50%, 40%, 30%, 20%, 10%, 5%, 2%, 1%, or less.

An antigen binding site is generally formed by the variable heavy (VH) and variable light (VL) immunoglobulin domains, with the antigen-binding interface formed by six surface polypeptide loops, termed complementarity determining regions (CDRs). There are three CDRs in each VH (HCDR1, HCDR2, HCDR3) and in each VL (LCDR1, LCDR2, LCDR3), together with framework regions (FRs).

Typically, a VH domain is paired with a VL domain to provide an antibody antigen-binding site, although a VH or VL domain alone may be used to bind antigen. The VH domain (e.g. from sequences 1) may be paired with the VL domain (e.g. from sequences 2), so that an antibody antigen-binding site is formed comprising both the VH and VL domains. Analogous embodiments are provided for the other VH and VL domains disclosed herein. In other embodiments, VH chains in sequences 1 are paired with a heterologous VL domain. Light-chain promiscuity is well established in the art. Again, analogous embodiments are provided by the invention for the other VH and VL domains disclosed herein. Thus, the VH of the parent or of any of antibodies chain on sequences 2 may be paired with the VL of the parent or of any of antibodies on sequences 1 and 2, or other antibody.

An antigen binding site may comprise a set of H and/or L CDRs of the parent antibody or any of antibodies in sequences 1 and 2 with as many as twenty, sixteen, ten, nine or fewer, e.g. one, two, three, four or five, amino acid additions, substitutions, deletions, and/or insertions within the disclosed set of H and/or L CDRs. Such modifications may potentially be made at any residue within the set of CDRs.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various mutant proteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton et at. Nature 354:105 (1991), which are each incorporated herein by reference.

A further aspect of the invention is an antibody molecule comprising a VH domain that has at least about 60, 70, 80, 85, 90, 95, 98, or about 99% amino acid sequence identity with a VH domain of any of antibodies listed in sequences 1, the appended sequence listing or described herein, or with an HCDR (e.g., HCDR1, HCDR2, or HCDR3) shown in sequences 1. The antibody molecule may optionally also comprise a VL domain that has at least 60, 70, 80, 85, 90, 95, 98, or 99% amino acid sequence identity with a VL domain of any of the antibodies shown in sequences 2, the appended sequence listing or described herein, or with an LCDR (e.g., LCDR1, LCDR2, or LCDR3) shown in sequences 2. Algorithms that can be used to calculate % identity of two amino acid sequences comprise e.g. BLAST (Altschul, et al., (1990) J. Mol. Biol. 215: 405-410), FASTA (Pearson and Lipman (1988) PNAS USA 85: 2444-2448), or the Smith-Waterman algorithm (Smith and Waterman (1981) J. Mol. Biol. 147: 195-197), e.g. employing default parameters.

A further aspect of the invention is an antibody molecule comprising a VH domain that has at least about 60, 70, 80, 85, 90, 95, 98, or about 99% amino acid sequence identity with a VH domain of any of antibodies listed in sequences 1, or with an HCDR (e.g., HCDR1, HCDR2, or HCDR3) shown in sequences 1. The antibody molecule may optionally also comprise a VL domain that has at least 60, 70, 80, 85, 90, 95, 98, or 99% amino acid sequence identity with a VL domain of any of the antibodies shown in sequences 2, the appended sequence listing or described herein, or with an LCDR (e.g., LCDR1, LCDR2, or LCDR3) shown in sequences 2.

Variants of the VH and VL domains and CDRs of the present invention, including those for which amino acid sequences are set out herein, and which can be employed in targeting agents and antibodies for human ENO1 protein can be obtained by means of methods of sequence alteration or mutation and screening for antigen targeting with desired characteristics. Examples of desired characteristics include but are not limited to: increased binding affinity for antigen relative to known antibodies which are specific for the antigen; increased neutralization of an antigen activity relative to known antibodies which are specific for the antigen if the activity is known; specified competitive ability with a known antibody or ligand to the antigen at a specific molar ratio; ability to immunoprecipitate complex; ability to bind to a specified epitope; linear epitope, e.g. peptide sequence identified using peptide-binding scan as described herein, e.g. using peptides screened in linear and/or constrained conformation; conformational epitope, formed by non-continuous residues; ability to modulate a new biological activity of human ENO1 protein or downstream molecule. Such methods are also provided herein.

A further aspect of the present invention relates to a targeted binding agent (i.e. an antibody) including those for which amino acid sequences that binds to the epitope peptide comprising amino acid sequence that has at least about 60, 70, 80, 85, 90, or about 92% amino acid sequence identity listed in sequences 9 or 10 on human ENO1 protein and can be used to treat an human ENO1 protein disease or disorder. A human ENO1 protein-related disease or disorder can be any condition arising due to the aberrant activation or expression of human ENO1 protein. In one example, the human ENO1 protein-related disease is a neoplastic disease such as non-small cell lung cancer, hepatocellular (liver) carcinoma, gastric (stomach) cancer, breast cancer, pancreatic duct adenocarcinoma.

Variants of antibody molecules disclosed herein may be produced and used in the present invention. Following the lead of computational chemistry in applying multivariate data analysis techniques to the structure/property-activity relationships (Wold, et al., Multivariate data analysis in chemistry. Chemometrics—Mathematics and Statistics in Chemistry (Ed.: B. Kowalski), D. Reidel Publishing Company, Dordrecht, Holland, 1984) quantitative activity-property relationships of antibodies can be derived using well-known mathematical techniques, such as statistical regression, pattern recognition and classification (Norman et al., Applied Regression Analysis. Wiley-Interscience; 3rd edition (April 1998); Kandel, Abraham & Backer, Eric. Computer-Assisted Reasoning in Cluster Analysis. Prentice Hall PTR, (May 11, 1995); Krzanowski, Wojtek. Principles of Multivariate Analysis: A User's Perspective (Oxford Statistical Science Series, No 22 (Paper)). Oxford University Press; (December 2000); Witten, Ian H. & Frank, Eibe. Data Mining: Practical Machine Learning Tools and Techniques with Java Implementations. Morgan Kaufmann; (Oct. 11, 1999); Denison David G. T. (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002); Ghose, Amp K. & Viswanadhan, Vellarkad N. Combinatorial Library Design and Evaluation Principles, Software, Tools, and Applications in Drug Discovery). The properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions.

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments. In a structural approach, a model can be created of the antibody molecule using any freely available or commercial package, such as WAM. A protein visualization and analysis software package, such as Insight II (Accelrys, Inc.) or Deep View may then be used to evaluate possible substitutions at each position in the CDR. This information may then be used to make substitutions likely to have a minimal or beneficial effect on activity.

The techniques required to make substitutions within amino acid sequences of CDRs, antibody VH or VL domains and/or binding agents generally are available in the art. Variant sequences may be made, with substitutions that may or may not be predicted to have a minimal or beneficial effect on activity, and tested for ability to bind and/or neutralize and/or for any other desired property.

Variable domain amino acid sequence variants of any of the VH and VL domains whose sequences are specifically disclosed herein may be employed in accordance with the present invention, as discussed.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least about 5, 6, 8, or 10 amino acids long, preferably at least about 14 amino acids long, more preferably at least about 20 amino acids long, usually at least about 50 amino acids long, and even more preferably at least about 70 amino acids long. The term "analog" as used herein refers to polypeptides which are comprised of a segment of at least about 25 amino acids that has substantial identity to a portion of a deduced amino acid sequence and which has at least one of the following properties: (1) specific binding to human ENO1 protein under suitable binding conditions, (2) ability to block appropriate ligand/ENO1 protein binding, or (3) ability to inhibit ENO1 protein activity. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

As used herein, the term "antibody" refers to a polypeptide or group of polypeptides that are comprised of at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site.

As used herein, a "targeted binding agent" is an agent, e.g. antibody, or binding fragment thereof, that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope. As described below, a targeted binding agent may comprise at least one antigen binding domain of an antibody, wherein said domain is fused or contained within a heterologous protein.

"Binding fragments" of an antibody are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counter-receptor by at least about 20%, 40%, 60%, or 80%, and more usually greater than about 85% (as measured in an in vitro competitive binding assay).

An antibody may be oligoclonal, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody, an anti-idiotypic antibody and antibodies that can be labeled in soluble or bound form as well as fragments, variants or derivatives thereof, either alone or in combination with other amino acid sequences provided by known techniques. An antibody may be from any species. The term antibody also includes binding fragments of the antibodies of the invention; exemplary fragments include Fv, Fab, Fab', single stranded antibody (svFC), dimeric variable region (Diabody) and disulfide stabilized variable region (dsFv).

It has been shown that fragments of a whole antibody can perform the function of binding antigens. Examples of binding fragments are (Ward, E. S. et al., (1989) Nature 341, 544-546) the Fab fragment consisting of VL, VH, CL and CH1 domains; (McCafferty, et al., (1990) Nature, 348, 552-554) the Fd fragment consisting of the VH and CH1 domains; (Holt, et al., (2003) Trends in Biotechnology 21, 484-490) the Fv fragment consisting of the VL and VH domains of a single antibody; (iv) the dAb fragment (Ward, E. S., et al., Nature 341, 544-546 (1989), McCafferty, et al., (1990) Nature, 348, 552-554, Holt, et al., (2003) Trends in Biotechnology 21, 484-490], which consists of a VH or a VL domain; (v) isolated CDR regions; (vi) F(ab').sub.2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird, et al., (1988) Science, 242, 423-426, Huston, et al., (1988) PNAS USA, 85, 5879-5883); (viii) bispecific single chain Fv dimers (PCT/US92/09965) and (ix) "diabodies", multivalent or multispecific fragments constructed by gene fusion (WO94/13804; Holliger, P. (1993), et al., Proc. Natl. Acad. Sci. USA 90 6444-6448). Fv, scFv or diabody molecules may be stabilized by the incorporation of disulfide bridges linking the VH and VL domains (Reiter, Y. et al., Nature Biotech, 14, 1239-1245, 1996). Minibodies comprising a scFv joined to a CH3 domain may also be made (Hu, S., et al., (1996) Cancer Res., 56, 3055-3061). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

The term "epitope" includes any protein determinant capable of specific binding to an immunoglobulin or T-cell receptor. Epitope determinants usually consist of chemically active surface groupings of molecules such as amino acids or sugar side chains and may, but not always, have specific three-dimensional structural characteristics, as well as specific charge characteristics. An antibody is said to specifically bind an antigen when the dissociation constant is ≤1 micro M, preferably ≤100 nM, and most preferably ≤10 nM.

The term "agent" is used herein to denote a chemical compound, a mixture of chemical compounds, a biological macromolecule, or an extract made from biological materials.

"Active" or "activity" in regard to an ENO1 polypeptide refers to a portion of an ENO1 polypeptide that has a biological or an immunological activity of a native ENO1 polypeptide. "Biological" when used herein refers to a biological function that results from the activity of the native ENO1 polypeptide. A preferred ENO1 biological activity includes, for example, ENO1 induced the plasminogen activity.

"Mammal" when used herein refers to any animal that is considered a mammal. Preferably, the mammal is human.

Digestion of antibodies with the enzyme, papain, results in two identical antigen-binding fragments, known also as "Fab" fragments, and a "Fe" fragment, having no antigen-binding activity but having the ability to crystallize. Digestion of antibodies with the enzyme, pepsin, results in the a F(ab')2 fragment in which the two arms of the antibody molecule remain linked and comprise two-antigen binding sites. The F(ab')$_2$ fragment has the ability to crosslink antigen.

"Fv" when used herein refers to the minimum fragment of an antibody that retains both antigen-recognition and antigen-binding sites. "Fab" when used herein refers to a fragment of an antibody that comprises the constant domain of the light chain and the CH1 domain of the heavy chain. The term "mAb" refers to monoclonal antibody.

The term "pharmaceutical agent or drug" as used herein refers to a chemical compound or composition capable of inducing a desired therapeutic effect when properly administered to a patient. Other chemistry terms herein are used according to conventional usage in the art, as exemplified by The McGraw-Hill Dictionary of Chemical Terms (Parker, S., Ed., McGraw-Hill, San Francisco (1985)), (incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" includes human and veterinary subjects.

As used herein, the term "monitoring" refers to the process of detecting and/or observing the development of cancer by determining the abundance of ENO1 protein in cancer cells.

Methods for determining the abundance of ENO1 include, but are not limited to, measuring the binding of ENO1 proteins and ENO1-specific antibodies, Western blotting, flow cytometry, immunohistochemistry (IHC), RT-PCR, and/or microarray analysis.

EXAMPLES

The practice of the present invention may employ technologies comprising conventional techniques of cell biology, cell culture, antibody technology, and genetic engineering, which are within the ordinary skills of the art. Such techniques are explained fully in the literature.

The following examples illustrate the development and use of ENO1-specific antibodies to suppress tumor growth by inducing an anti-ENO1 immune response.

Example 1

The ENO1 Binding ELISA of EN10 mAb Antibody

To evaluate the ENO1 binding affinity of anti-human ENO1 antibody EN10 mAb, the hybridomas were grown in RPMI containing 10% fetal calf serum (FCS). After one week culture, $1 \times 10^6$ cells were collected, washed with PBS, resuspended in 200 ul RPMI medium, and injected into severe combined immunodeficiency (SCID) mice by IP injection. Three weeks later, acites of mice was collected and diluted to 15 ml. Antibody was further purified by 40% ammonium sulfate and Protein A column (Montage antibody purification kit Millipore). The purified antibody was concentrated with an Amicon Ultra-15 centrifugal filter device, following the protocols provided by the manufacturer (Millpore). The purity of antibody was analyzed by 12% SDS PAGE.

Four hundred (400) ng of human ENOL protein was coated on a 96-well ELISA plate, and the plate was further washed with PBS. Serial dilutions from $1 \times 10^{-12}$ to $1 \times 10^{-8}$ M of EN10 mAb antibody were added to the plate, and the plate was incubated at 37° C. for 1 hour. A goat anti-mouse IgG conjugated with hypoxanthine phosphoribosyltransferase (HPRT) was added. After 1 hour, 3,3',5,5'-Tetramethylbenzidine (TMB) was added and OD405 was read. Every study was repeated three times. Data were presented as mean±SD. OD readings and concentrations of antibodies were used to make a multiple scatter plot using Sigmaplot. The $K_d$ values were predicted by four parameter logistic fit.

The results of this experiment are shown in FIG. 1. Antibody EN10 mAb had productivities from 20.4 mg to 4.6 mg per mice. The Kd value of EN10 mAb antibody was $2.03\pm0.12\times10^{-10}$ M (N=3). This result indicates that EN10 mAb antibody can recognize the human ENO1 protein and has a favor affinity with a Kd value of about $2.03\pm0.12\times10^{-10}$ M (N=3).

Example 2

To assess the capability of EN10 mAb to inhibit the ENO1 plasminogen receptor activity of cancer cells, a human lymphoma U937 cell line was grown in RPMI containing 10% FCS. Cells were treated with 10 microgram/ml of LPS for 6 hours to induce ENO1 protein expression on the cell surface. $1.5\times10^6$ cells/ml in PBS were then pre-incubated with 1 microgram/ml human Lys-plasminogen and 10 microgram/ml of EN10 mAb for one hour, respectively. Samples were washed with PBS twice and 3 nM of tissue specific plasminogen activator and 0.5 mM of chromogenic substrate S-2251 were added. After one hour incubation at 37° C., OD 405 was read. Every study was repeated three times, and the antagonist activity was analyzed. Data were presented as mean±SD. T-test was used to compare each group. P values <0.05 were considered statistically significant.

Figure 2:
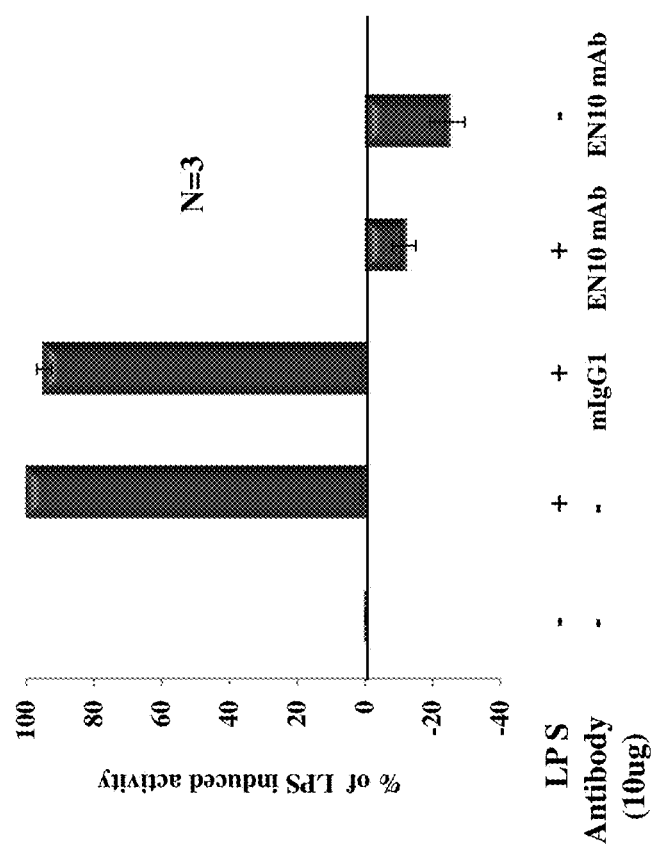
FIG. 2 shows the results of U937 fibrinolytic assay of EN10 mAb. The induction of ENO1 expression by LPS in human U937 lymphoma cell line and the plasmin activity assay were performed as described in Example 2. These result show that EN10 mAb alleviate the plasminogen receptor activities of inducible ENO1 protein.

Results of this experiment are shown in FIG. 2. EN10 mAb had a high ENO1 plasminogen receptor antagonist activity and can achieve 100% inhibition of LPS-induced specific ENO1 activity. Therefore, EN10 mAb would have a good potential in inhibiting the transmigration of cancer cells to the target organs.

Example 3

The result of Example 2 suggests that EN10 mAb can inhibit the ENO1 plasminogen receptor activity. The inhibition of ENO1 plasminogen receptor activity may result in the inhibition of plasminogen activation and transmigration activity in the LPS-stimulated human U937 lymphoma cell line.

To assess whether compromising the ENO1 plasminogen receptor activity results in the alleviation of invasion activity of cancer cells, a human lymphoma U937 cell line was grown in RPMI containing 10% FCS. Cells were treated with 10 microgram/ml of LPS for 6 hours to induce ENO1 protein expression on cell surface. After being mixed with 5 to 50 microgram/ml of EN10 mAb, $2\times10^4$ cells were seeded in the top chamber of a two-chamber assay system containing 15 micro molar of Lys-plasminogen and incubated for 24 hours with media containing 10% FBS and 10 nM MCP-1 in the lower chamber. An anti-mouse IgG was used as a negative control group. Two chambers were separated by a micropore filter (8 micrometer pore size) coated with matrigel. After the incubation period, cells in the lower chamber were counted by a hemocytometer under a microscope. Every study was repeated three times. Data are presented as mean±SD. T-test was used to compare each groups. P values <0.05 were considered statistically significant.

Figure 3:
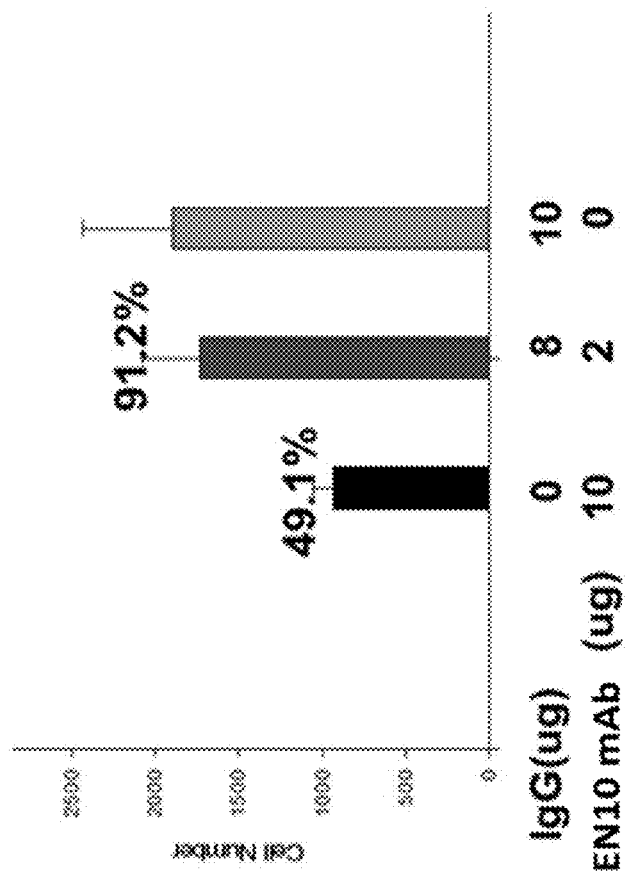
FIG. 3 shows results of invasion activities of U937 cells treated with different concentrations of EN10 mAb isolated from hybridoma, after the surface ENO1 expression of cells was induced by LPS. Detailed procedures were performed as described in Example 3. These data show that the EN10 mAb inhibits the invasion activity of U937 cells in a dose-dependent manner.

The results are shown in FIG. 3. When LPS-treated U937 cells were treated with 5 to 50 microgram/ml of EN10 mAb, the invasion activity of U937 was from 90.2±2% to 49.1±1% (N=3) of the control IgG. These results indicate that EN10 mAb can alleviate the invasion capability of activated U937 by compromising the ENO1 plasminogen receptor activity in a dose-dependent manner. By targeting ENO1 protein on the surface of lymphoma, it is feasible to inhibit cells entering affected sites using EN10 mAb.

Example 4

EN10 mAb Recognizes the Surface ENO1 of U937 Lymphoma Cell Line Stimulated by LPS Human U937 lymphoma cells were grown in RPMI containing 10% FCS. Cells were treated with 10 microgram/ml of LPS for 6 hours to induce ENO1 protein expression on the cell surface. For flow cytometric analysis, the intact whole cells were stained with or without EN10 mAb (1:300 dilution), visualized with FITC-conjugated goat antiserum (Jackson Lab), and analyzed with FACScan flow cytometer (Becton Dickinson). ENO1 expression was measured by the resulting fluorescence intensity.

Figure 4:
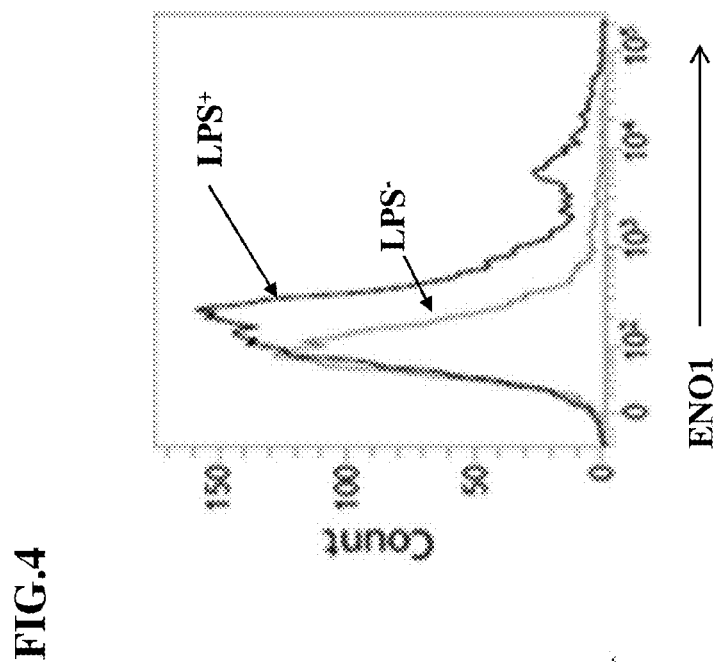
FIG. 4 shows that EN10 mAb recognizes the cell surface ENO1 on U937 cells treated with LPS. Detailed procedures were performed as described in Example 4. The histogram indicates that ENO1 is high expressed in the surface of U937 after cells were administrated with LPS.

Results from these experiments are shown in FIG. 4. Incubating U937 with LPS and EN10 mAb shifts the histogram to the right, as compared to incubating the cells without LPS but with EN10 mAb. This result indicates that U937 cells increase in expressing ENO1 on their cell surfaces when cells are treated with LPS. These data support the notion that EN10 mAb recognizes LSP-induced surface ENO1 on the lymphoma cells.

Example 5

Cloning of the Gene Encoding the Antibody EN10 mAb was Performed in Accordance With the Methods Described Below (1) cDNA Cloning of Antibody Genes and Preparation The hybridoma was cultured in a RPMI medium (manufactured by Gibco) containing 10% FCS. After the cell number reached about $10\times10^6$/ml, the cells were collected by centrifugation, and then TRIzol® (manufactured by Invitrogen) was added to extract total RNA in accordance the instruction manual. Cloning of the variable region of the antibody cDNAs was performed using a mouse Ig-primer set (manufactured by Novagen) in accordance with the attached instruction manual.

(a) The synthesis of 1st Strand cDNA was performed in accordance with the instruction manual of SuperScript® III First-Strand Synthesis System (manufactured by Invitrogen).

The 1st strand cDNA was prepared using 5 microgram of the total RNA as a template. Five micrograms of total hybridoma RNA, 1 microL of 50 ng/microL of random primers, and 1 microL of 10 mM dNTP were mixed, and DEPC-treated water was added to 10 microL in a 200 microL PCR tube. The reaction mixture was incubated at 65° C. for 5 min, and then placed on ice for at least 1 minute. Ten microL of cDNA Synthesis Mixture containing 2 microL of 10× RT buffer, 4 microL of 25 mM MgCl$_2$, 2 microL of DTT, 1 microL of 4 unit RNaseOUT™, and 1 microL of 200 unit SuperScript® III RT were added, mixed gently, and collected by brief centrifugation. The reaction tube was incubated for 10 min at 25° C. and followed by 50 min at 50° C. The reaction was terminated at 85° C. for 5 min and chilled on ice. The tube was briefly centrifuged to collect the reaction, and 1 microL of RNase H was added and incubated for 20 min at 37° C.

(b) Amplification by PCR of Heavy Chain Genes and Light Chain Genes

A reaction solution having a composition of 5 microL of cDNA, 5 microL of 10× reaction Buffer, 1 microL of 10 mM dNTP mix, 1 microL of 2.5 unit Taq polymerase, and 1 microL of forward primer 1 and 1 microL of reverse primer 2 provided by the primer set was prepared in a final volume of 50 microL with double distilled water and subjected to PCR.

For amplification of the light chain and heavy chain of an antibody, a cycle of 94 degree C. for 10 minutes was used, then a cycle of 94 degree C. for one minute, 52 degree C. for one minute, and 72 degree C. for 1 minute was repeated 35 times, and the reaction was incubated at 72 degree C. for 10 more minutes. The reaction solution was subjected to 2% agarose gel electrophoresis to analyze the reaction products. Products with the correct molecular weights, about 463 bps for the heavy chain and 451 bps for the light chain, were ligated to a pCR 2.1-TOPO vector (manufactured by Invitrogen) for subcloning in accordance with the attached instruction manual. M13 forward (5'-GTAAACAAC GACGGCGAG-3' (SEQ ID NO:12) and M13 reverse (5'-CAG GAA ACA GCT ATG AC-3' (SEQ ID NO:13)) primers were then used to determine the nucleotide sequence. Based on the sequence information, antibody sequences were translated into proteins sequences by ExPASY-Translation Tool. Resulting sequences of EN10 mAb comprise a heavy chain amino acid sequence and a light chain sequence having complementarity determining regions (CDR), which were determined by the method published by Kabat et al., Sequences of Proteins of Immunological Interest, Fifth Edition, NIH Publication 91-3242, Bethesda Md. (1991), Vols. 1-3.

FIG. 5A depicts the variable heavy chain region/domain amino acid sequence of EN10 mAb (SEQ ID NO: 1). The framework regions (FR1, FR2, FR3, and FR4) and CDRs (HCDR1 (SEQ ID NO: 3), HCDR2 (SEQ ID NO: 4), and HCDR3 (SEQ ID NO: 5)) are indicated.

FIG. 5B depicts the variable light chain region/domain amino acid sequences of EN10 mAb (SEQ ID NO: 2). The framework regions (FR1, FR2, FR3, and FR4) and CDRs (LCDR1 (SEQ ID NO: 6), LCDR2 (SEQ ID NO: 7), and LCDR3 (SEQ ID NO: 8)) are indicated.

Example 6

Humanization of EN10 mAb

Selection of Human V Region Framework Sequences

Using mouse monoclonal antibody EN10 mAb as the parent antibody, EN10 mAb CDR sequences according to the Kabat definitions were described in the FIGS. 5A and 5B (SEQ ID NO: 1 and SEQ ID NO: 2).

For humanized EN10 (abbreviated as: hum EN10) mAb 4D5, the human acceptor framework was selected from database or utilizing a framework that has been validated in the clinic. Human heavy and light chain framework sequences in the VH subgroup III, IGHV3-66*04 (SEQ ID NO: 10 and VL κ subgroup I, IGKV1-39*01 (SEQ ID NO: 9) (FIG. 6A) have been validated in the clinic and have been used in many humanized antibodies with success.

For hum EN10 mAb IMGT, human germ-line VL and VH sequences with the highest degree of homology with the EN10 mAb framework regions were identified from the IMGT database (the International immunogenetics Information System®). The homology searches may be performed with BLAST or similar methods. The EN10 mAb variable region sequences used as query sequences are available from the literature, such as U.S. patent application Ser. No. 14/142,186.

Human heavy chain framework sequences in the VH subgroup III (VH3) have been used in many humanized antibodies with success, and human light chain framework sequences of the VL κ subgroup II (Vκ2) are also shown to be good candidates. Therefore, the framework sequences of VHIII and Vκ2 subgroups were selected for the search for VH and VL frameworks, respectively. These searches identified IGHV3-72*01 and IGKV2D-29*02, respectively, as the VH and VL sequences most homologous to the corresponding heavy chain and light chain framework sequences in EN10 mAb.

As shown in FIG. 6B, the sequences of IGHV1-18*01 human heavy chain framework regions differ from those in EN10 mAb by 19 amino acids (the underlined residues), which corresponds to a 24.69% (20/81 total residues in the framework regions) variation. The human light chain (kappa I subtype) framework sequences, as shown in FIG. 6B, differ from the sequences in IGKV12-44*01 of EN10 mAb by 15 amino acids (the underlined residues), which corresponds to a 19.73% (15/76 total residues in the framework regions) variation.

Even with these degrees of variations in the framework regions, scFv fragments, generated by grafting CDR sequences from EN10 mAb into the identified human heavy-chain and light-chain framework sequences, have relatively good affinities for ENO1 (KD=about $10^{-11}$ M) (see Table I below). These results suggest that the framework regions can tolerate a relatively high degree of variations without impacting the CDR region conformations.

TABLE I

| ENO1 Binding ELISA of EN10 chimera and Hum EN10 IMGT | | |
|---|---|---|
| | Mouse chimera | Hum EN10 IMGT |
| KD (M) | 3.33E−11 | 3.65E−11 |

These two pairs of light chain and heavy chain sequences (hum 4D5 and hum IMGT) will be used as examples for the construction of humanized antibodies against human ENO1.

Example 7

Binding Affinity Analysis of Humanized Antibodies

Figure 7A:
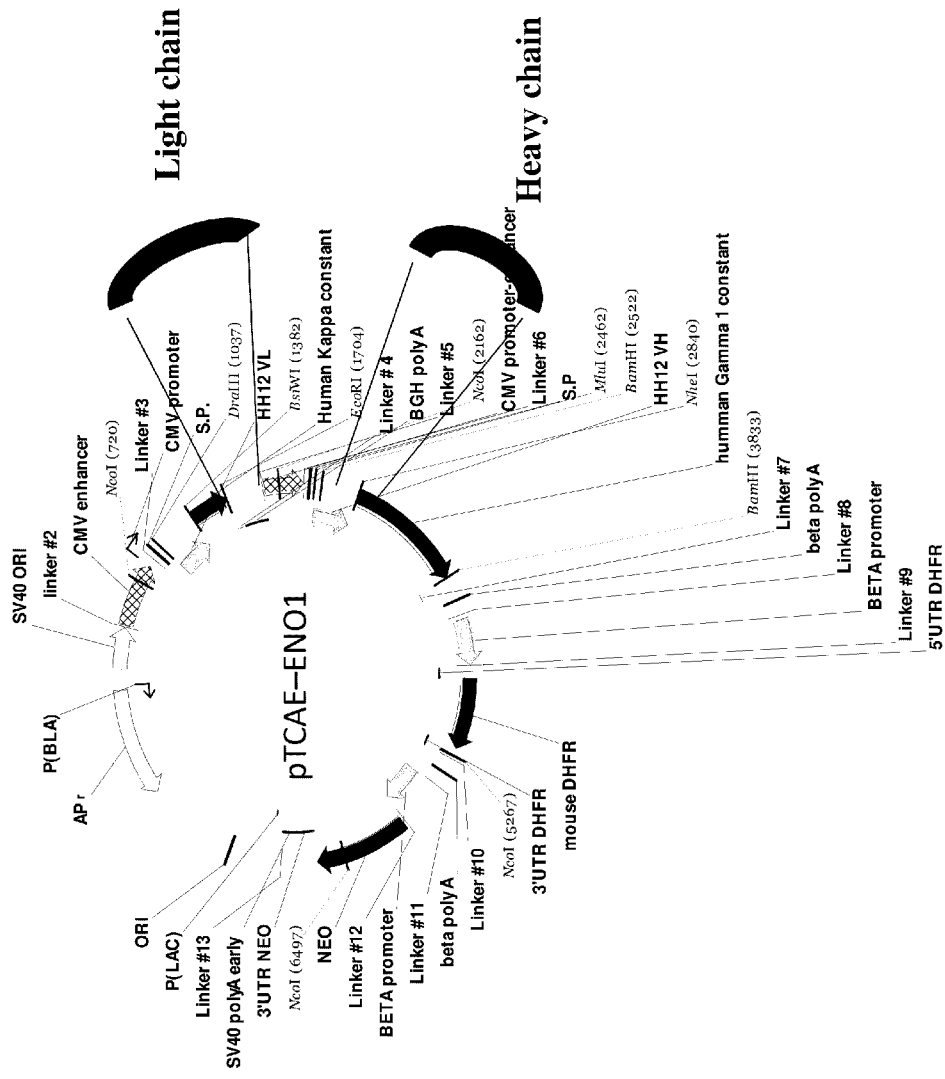
FIG. 7A shows an expression vector for the generation of mouse-human chimera and humanized editions of EN10 mAb. The detailed procedures for the purification of the different EN10 mAb editions of antibodies are described in Example 7.

To confirm the affinity change after the mouse antibodies was humanized, the variable regions of humanized light chain and humanized heavy chains of IMGT and 4D5 versions were directly generated by the nucleotide synthesis method, respectively. The mouse variable region, humanized edition of IMGT and 4D5 variable regions and a human Fc chimera antibody expression vector pTCAE8-ENO1, as shown in FIG. 7A, were introduced into host cells to prepare recombinant antibody-expressing cells. As the host cells for expression, the FreeStyle293 cells (manufactured by Invitrogen) were used. The vector was introduced into the host cells by lipofectamine 2000 in accordance with the attached instruction manual (manufactured by Invitrogen.) About 2.5 microgram of the antibody expression vector was linearized by restriction enzymes, the gene was introduced into $4\times10^6$ cells, and cells were inoculated to a 6-well culture plate. The agent corresponding to a selection marker of the expression vector was added, and cells were continuously cultured to form a stable pool.

A culture supernatant containing human IgG antibody was prepared by the method described below. The antibody-producing cells were acclimated in a Free Style™ 293 Expression Medium (GIBCO). The cells were cultured in a tissue culture flask, and the culture supernatant was collected when the viable rate of the cells was 90%. The collected supernatant was filtered through 10 micrometer and 0.2 micrometer filters (manufactured by Millpore) to remove contaminants. The culture supernatant containing the antibody was affinity-purified using Protein A (manufactured by Millipore), PBS as an absorption buffer, and 20 mM sodium citrate buffer (pH 3.0) as an elution buffer. The elution fractions were adjusted to around pH 6.0 by adding 50 mM sodium phosphate buffer (pH 7.0). The prepared antibody solution was replaced with PBS using a dialysis membrane (10,000 MW cut, manufactured by Spectrum Laboratories) and filter-sterilized through a membrane filter (manufactured by Millpore) having a pore size of 0.22 micrometer to yield the purified antibody. The concentration of the purified antibody was determined by measuring the absorbance at 280 nm and converting the measured value based on 1.45 optimal density equaling 1 mg/ml.

To know the biding kinetics difference among individual antibodies, surface plasmon resonance (SPR) measurement with a BIAcore 2000 (BIAcore, Inc., Piscataway, N.J.) was used as previously described (Karlsson & Falt, (1997) J. Immunol Methods 200:121-133). Carboxymethylated dextran biosensor chips (CMS, BIAcore Inc.) were activated with N-ethyl-N'-(3-dimethylaminopropyl)-carbodiimide hydrochloride (EDC) and N-hydroxysuccinimide (NHS) according to the supplier's instructions. Chimera EN10 mAb was diluted with 10 mM sodium acetate, pH 4.8, into 5 microgram/ml before injection at a flow rate of 20 micro L/minute to achieve approximately 100 response units (RU) of coupled protein followed by the injection of 1M ethanolamine to block unreacted groups. For kinetics measurements, two-fold serial dilutions of ENO1 (0.3125 nM to 40 nM) were injected in HBS-P Biacore running buffer provided by the manufacturer (BIAcore, Inc., Piscataway, N.J.) at 25 degree C. at a flow rate of 25 microL/min, and binding responses on the EN10 mAb were corrected by subtraction of responses on a blank flow cell. Association rates (kon or ka) and dissociation rates (koff or kd) were calculated using a simple one-to-one Langmuir binding model with separate fittings of kon and koff was used. (BIAcore™ Evaluation Software version 3.2).

Figure 7B:
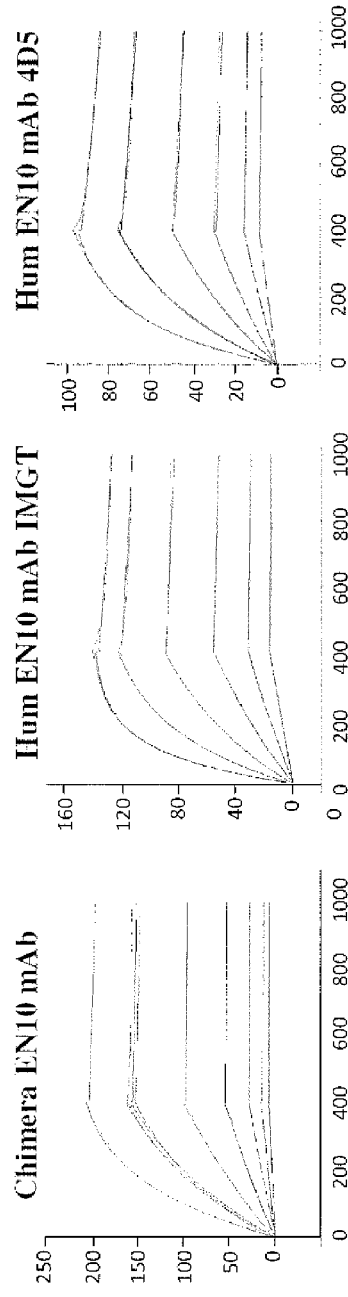
FIG. 7B depicts results from using the chimera EN10, hum EN10 mAb 4D5 and humEN10 mAb IMGT antibodies to determine binding affinity and kinetic constants of EN10 mAb. Detailed procedures of chimera antibody expression, purification and Kd analysis were performed as described in Example 7. The result Kd of hum EN10 mAb IMGT is not significant to that of mouse-human chimera EN10mAb.

The results are shown in the FIG. 7B and Table II. The kon and koff of chimera EN10 mAb binding with ENO1 are $3.57\times10^5$ and $8.271\times10^{-5}$, respectively, and Kd is $2.313\times10^{-10}$ mol/L. The kon and koff of hum EN10 mAb IMGT binding with ENO1 are $5.31\times10^5$ and $1.162\times10^{-5}$, respectively, and Kd is $2.188\times10^{-10}$ mol/L. For the 4D5 humanized edition, the kon and koff are $3.511\times10^5$ and $1.755\times10^{-5}$, respectively, and Kd is $4.997\times10^{-10}$ mol/L From FIG. of 7B and Table II, results suggest that all of humanized EN10 antibodies can recognize the human ENO1 protein and after humanization, the affinity of IMGT edition is similar to that of mouse chimera antibody and has a favor affinity with a Kd value of about $2.188\pm0.12\times10^{-10}$ M (N=3). The Hum EN10 mAb 4D5 also has a similar affinity, $4.997\times10^{-10}$ M.

Example 8

Hum EN10 mAb 4D5 and Hum EN10 mAb IMGT Antibodies Inhibit the Plasminogen Receptor Activity Induced by LPS of U937

To assess the capability of hum EN10 mAb 4D5 mAb and hum EN10 mAb IMGT to inhibit the ENO1 plasminogen receptor activity of cancer cells, a human lymphoma U937 cell line was grown in RPMI containing 10% FCS. Cells were treated with 10 microgram/ml of LPS for 6 hours to induce ENO1 protein expression on the cell surface. $1.5\times10^6$ cells/ml in PBS were then pre-incubated with 1 microgram/ml human Lys-plasminogen and different concentrations of hum EN10 mAb 4D5 and hum EN10 mAb IMGT for one hour, respectively. Samples were washed with PBS twice and 3 nM of tissue specific plasminogen activator and 0.5 mM of chromogenic substrate S-2251 were added. After one hour incubation at 37° C., OD 405 was read. Every study was repeated three times, and the antagonist activity was analyzed. Data were presented as mean±SD. T-test was used to compare each group. P values <0.05 were considered statistically significant.

Figure 8A:
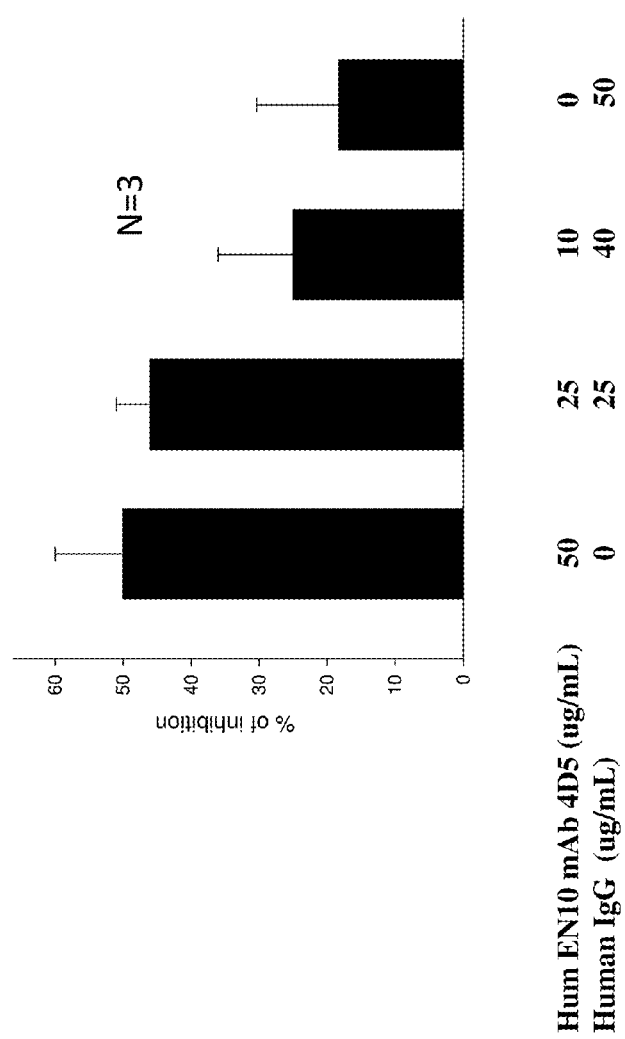
FIG. 8A and FIG. 8B depict results of U937 fibrinolytic assay of humEN10 mAb 4D5 and hum EN10 mAb IMGT antibodies. The induction of ENO1 expression by LPS in human U937 lymphoma cell line and the plasmin activity assay were performed as described in Example 2. Data show that the same as EN10 mAb both hum EN10 mAb 4D5 and hum EN10 mAb IMGT alleviate the plasminogen receptor activity of inducible ENO1 protein.
Figure 8B:
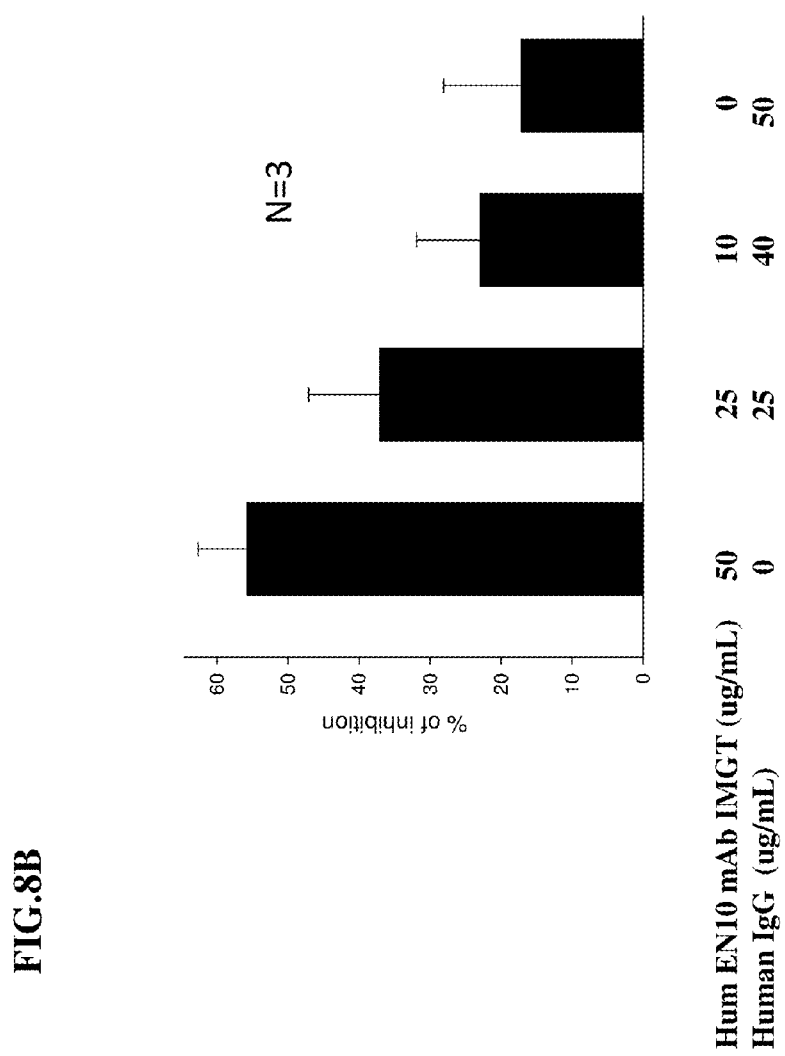

Results of this experiment are shown in FIG. 8A and FIG. 8B. The same as the parent antibody EN10 mAb, 50 microgram of both hum EN10 mAb 4D5 and hum EN10 mAb IMGT had high ENO1 plasminogen receptor antagonist activities and can achieve 50% and 56% inhibition of LPS-induced specific ENO1 activity and the inhibition percentage is dose-dependent. Therefore, both humanized antibodies would have a good potential in inhibiting the transmigration of cancer cells to the target organs.

Example 9

Hum EN10 mAb 4D5 and Hum EN10 mAb IMGT Antibodies Inhibit the Invasion Activity of U937

As results of example 8, humEN10 mAb 45D and EN10 mAb IMGT antibodies alleviate the inducible ENO1 plaminogen receptor activity of U937. This may result, as their patient antibody, in the inhibition of invasion activity of cancer cells.

To evaluate the anti-transmigration activity of hum EN10 mAb 4D5 and EN10 mAb IMGT, $3\times10^6$ of mouse brain endothelial bEnd.3 cells were precoated with matrix gel on upper chambers of the Cytoselect™ 24 Well Cell Migration and Invasion Assay kit in RPMI-1640 medium containing 10% fetal bovine serum for 24 h. The upper chambers were washed with PBS twice. RPMI medium containing 2% and 10% fetal bovine serum were added to upper and lower chambers, respectively. After mixing with 10, 50, and 100 microgram/ml of humEN10 mAb 4D5 and hum EN10 mAb IMGT, respectively, $2\times10^4$ cells of U937 were seeded in the top chamber of a two-chamber assay system and incubated for 24 hours and anti-human IgG was used as a negative control. Two chambers were separated by a micropore filter (8 μm pore size) coated with matrigel. After the incubation period, cells in the lower chamber were counted by a hemocytometer under a microscope. Each study was repeated three times. Data were presented as mean±SD.

T-test was used to compare activity between each group. P values <0.05 are considered statistically significant.

Figure 9A:
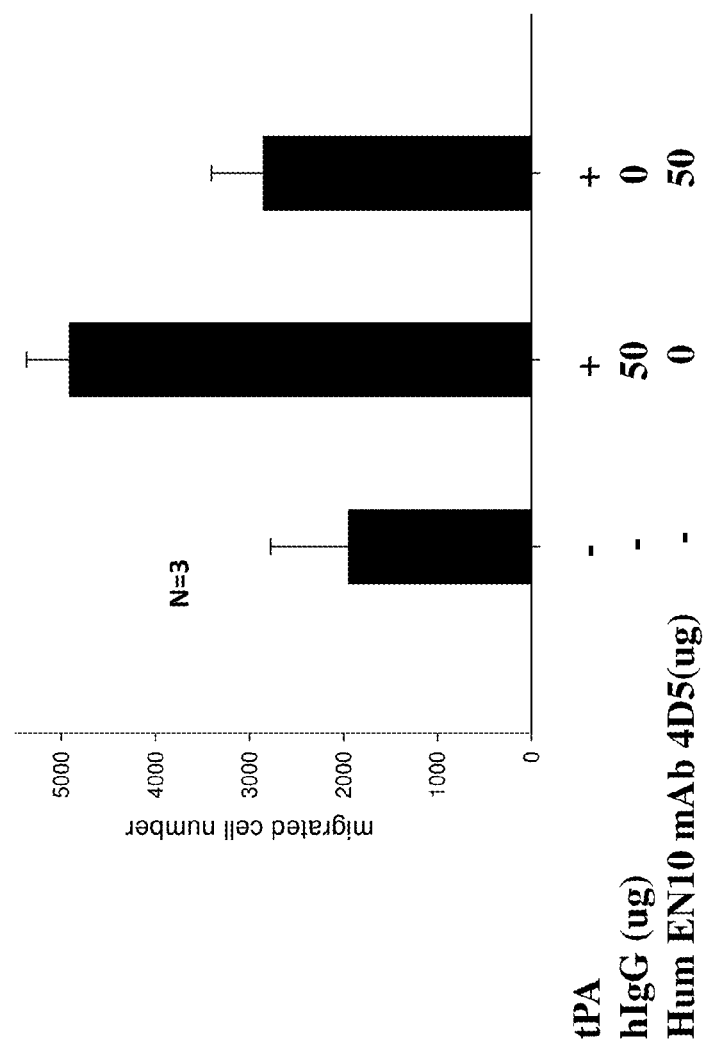
FIGS. 9A and 9B show results of invasion activities of U937 cells treated with different concentrations of humEN10 mAb 4D5 and humEN10 mAb IMGT antibodies, respectively, after the surface ENO1 expression of cells was induced by LPS. Detailed procedures were performed as described in Example 9. These data show that after humanization, the humEN10 mAb 4D5 and humEN10 mAb IMGT antibodies have activity to inhibit the invasion activity of U937 cells in a dose-dependent manner.
Figure 9B:
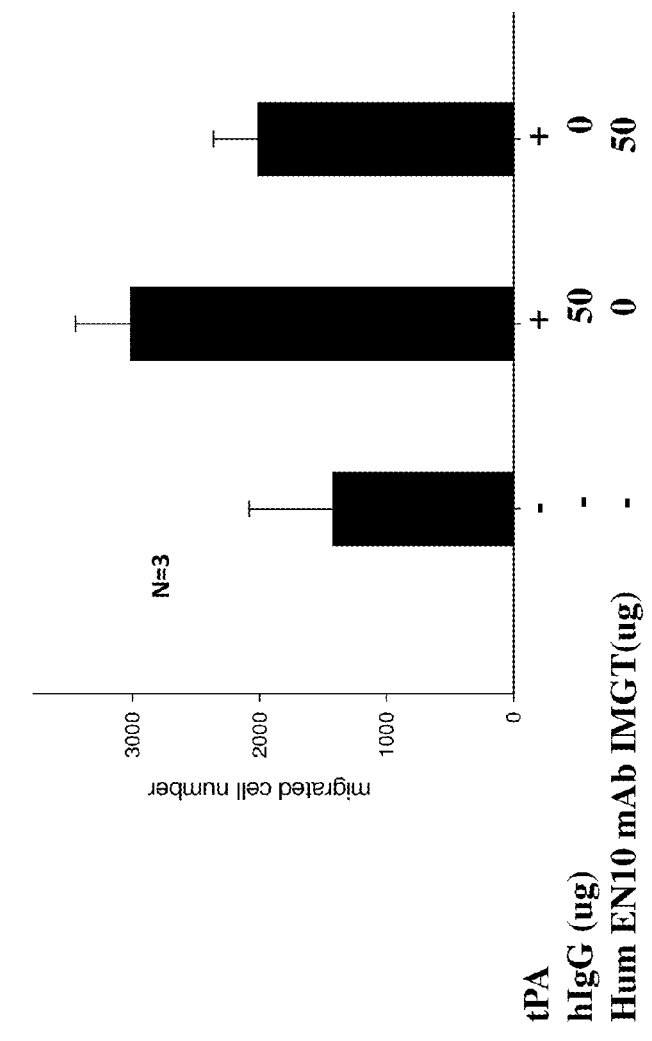

The results are shown in the FIGS. 9A and 9B. As in the study by Wang, et al, tPA stimulated the background invasion of U937 (FIGS. 8A and 8B). The invasion activity of U937 was inhibited about 41.8±11% (N=3) and 33±11% (N=3), when cells were administrated with 50 microgram per ml of hum EN10 mAb 45D and EN10 mAb IMGT antibodies, respectively (FIGS. 9A and 9B). These results are similar to those of Example 4. Both humanized antibodies have capability to inhibit the transmigration activity of U937 cells.

Example 10

Humanized EN10 mAb Inhibits the Dissociation of CL1-5 Cells From Collagen and Fibronectin To assess the signal transduction pathway between ENO1 plasminogen receptor-plasmin and extracellular substrates, 1 mg/ml of gelatin, 100 microgram/ml of fibrinogen, 10 microgram/ml of collagen and 10 microgram/ml of fibronectin, respectively, were coated on a non-treated ELISA plate overnight. CL1-5 cells (4×104 cells) were seeded on the plate, and 50 microgram/ml of hum EN10 mAb 4D5 was added to 200 µL of DMEM containing 10% FCS. Cells were incubated at 37° C. for 24 hours and then washed with PBS twice. 10% WST was added and reaction mixtures were incubated at 37° C. for 4 hours. The relative cell numbers in the plate were estimated by the reading of OD450. Each study was repeated three times. Data are presented as mean±SD. T-test was used to compare activity between each group. P values <0.05 are considered statistically significant.

Figure 10A:
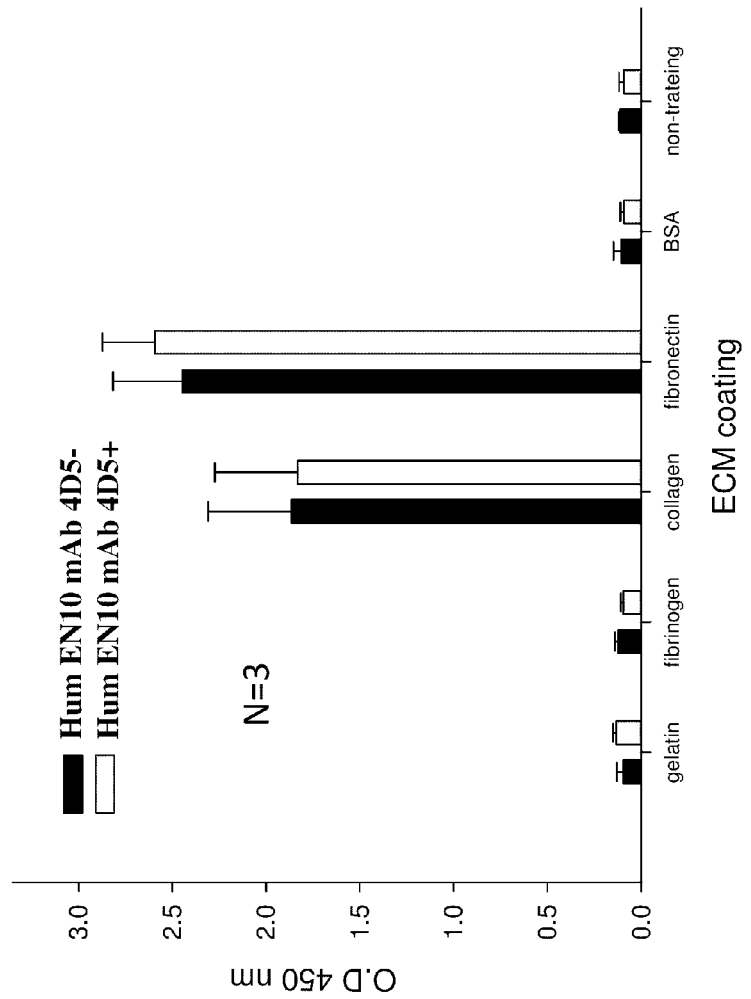
FIG. 10A shows the adhesion activity of CL1-5 lung carcinoma cells to matrix proteins. The adhesion assay was performed as described in Example 10. These data show that CL1-5 cells have higher adhesion activities to collagen and fibronectin.

Results from these experiments are shown in FIG. 10A. These data indicate that OD450 readings on fibronectin and collagen coated plates are 2.45±0.37 (N=3) and 1.83±0.44 (N=3). The readings are much higher than those of gelatin and fibrinogen plates, which are not significant different from the background reading. There are no significant difference between the hum EN10 mAb 4D5 treated group and the non-treated group. These results suggest that CL1-5 cells favor binding to fibronectin and collagen, and hum EN10 mAb 4D5 is not involved in the cell association pathway when cells are incubated in the medium without down-stream proteases, for example plasminogen and tPA. Data in FIG. 10A suggest that the ENO1 plasminogen receptor activity is not involved in the cell association pathway in the extracellular matrix. We further tested whether ENO1 takes part in the cell dissociation pathway in the extracellular matrix. One microgram/ml of fibronectin and 10 microgram/ml of collagen were, respectively, coated on a non-treated ELISA plate overnight. CL1-5 cells (4×10$^4$ cells) were seeded on the plate, and 0, 6.25, 12.5, 25, and 50 □ microgram/ml of hum EN10 mAb 4D5, respectively, were added to 200 micro L of DMEM containing 10% FCS. Furthermore, 10 microgram/mL Glu-plasminogen and 2 nM tPA were added. Cells were incubated at 37° C. for 24 hours and washed with PBS twice. Then, 10% WST was added and reaction mixtures were incubated at 37° C. for 4 hours. The relative cell numbers in the plate were estimated by the readings of OD450. Each study was repeated three times. Data are presented as mean±SD. T-test was used to compare activity between each group. P values <0.05 are considered statistically significant.

Figure 10B:
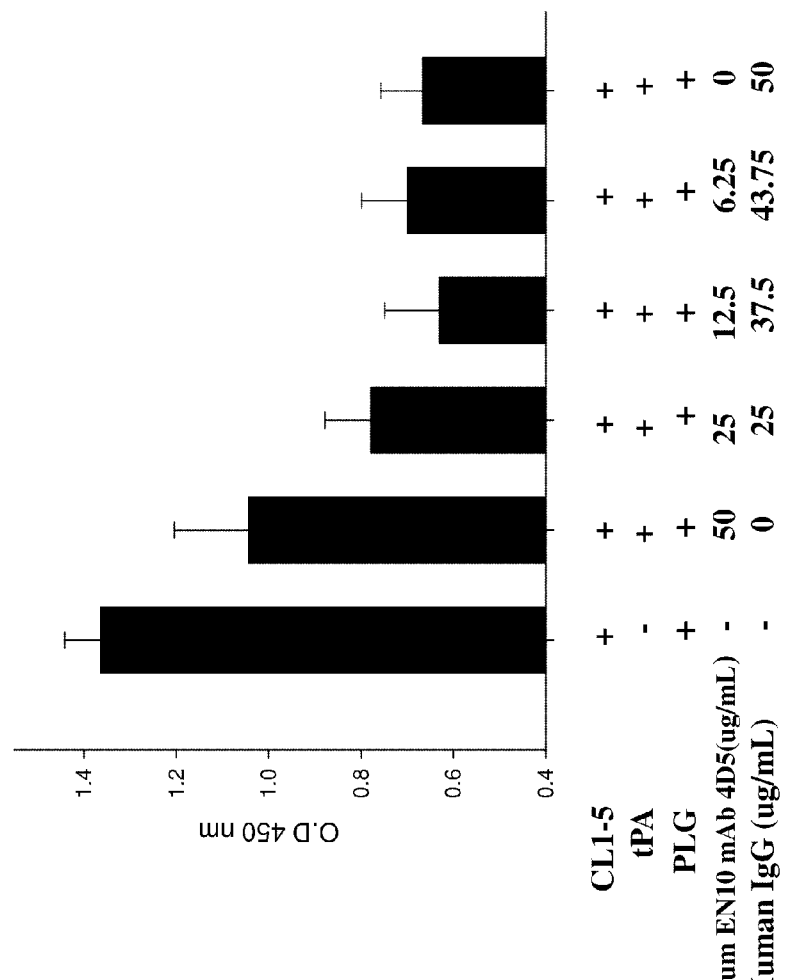
FIG. 10B shows results of inhibition of CL1-5 cell dissociation from fibronectin treated with the humEN10 mAb 4D5. The cell associated adhesion assay was performed as described in Example 10. These data show that the humEN10 mAb 4D5 inhibits the cell dissociation activity of CL1-5 from fibronectin in a dose-dependent manner.
Figure 10C:
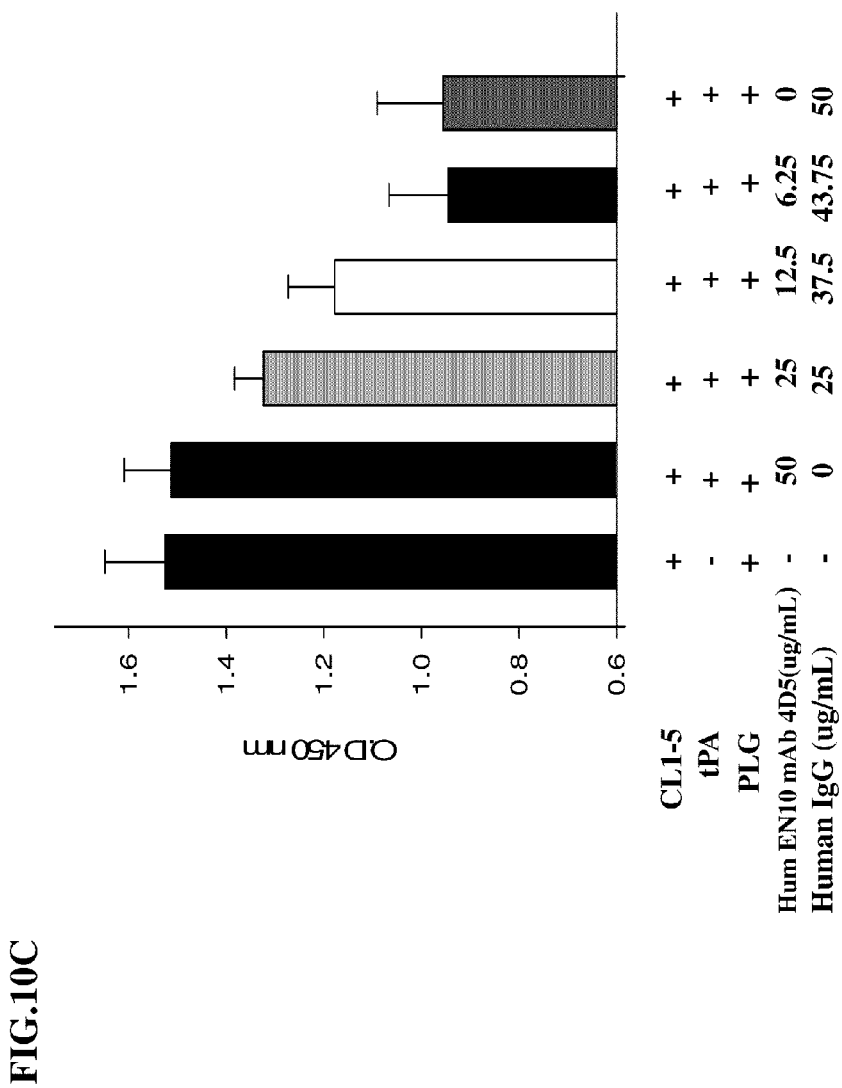
FIG. 10C shows results of inhibition of CL1-5 cell dissociation from collagen treated with the humEN10 mAb 4D5. The cell associated adhesion assay was performed as described in Example 10. These data show that the hum EN10 mAb 4D5 inhibits the cell dissociation activity of CL1-5 from collagen in a dose-dependent manner.

Results from these experiments are shown in FIG. 10B and FIG. 10C. The data indicate that cell numbers are directly proportional to the concentrations of treated hum EN10 mAb 4D5 in both extracellular matrices when the medium contains the ENO1 receptor down-stream proteases plasminogen and tPA. There are significant difference between 50 microgram hum EN10 mAb 4D5 treated group and the control IgG group (P<0.05) in both extracellular matrix studies. These results suggest that ENO1 is involved in the dissociation pathway of CL1-5 cells from extracellular matrixes, presumably by enhancing the plasmin and tPA protease activity. Hum EN10 mAb 4D5, functioning as an antagonist of ENO1, blocks the receptor activity of ENO1, resulting in the inhibition of plasmin and tPA activation and, therefore, inhibits the dissociation activity of CL1-5 cells from extracellular matrixes and invasion.

Example 11

Humanized ENO-1 Antibodies show the ADCC (antibody dependent cell cytotoxicity) effect on the Lung cancer cell line. It is known that in addition to the anti-growth inhibition, the ADCC of Herceptin is very important for its anti-tumor effect. Because hum EN10 mAb 4D5 and hum EN10 mAb IMGT antibodies have the same Fc fragment of Herceptin, we rationalized that both antibodies have the ADCC activity.

To test the ADCC effect of hum EN10 mAb 4D5 and Hum EN10 mAb IMGT antibodies against cancer cells, 2×10$^4$ of human lung CL1-5cancer cells were grown in 96 ELISA plates. After overnight incubation, different concentrations of hum EN10 mAb 4D5, hum EN10 mAb IMGT and the control IgG1 antibodies were added. Fresh blood samples from 5 volunteers were collected followed the IRB Guide line of DCB. PBMC (peripheral blood mononuclear cell) were prepared by Blood:PBS:FICOLL=1:1:1 solution under 3000 rpm centrifugation for 30 minutes. The resulting PBMC were collected and washed with PBS twice. PBMCs were suspended in RPMI1640 medium containing 5% FBS and diluted to the concentration with 2.5×10$^7$ cells/mL. Then 50 microliter of PBMC was added to the ELISA plates containing CL1-5. Cells were spun at 3000 rpm for 5 minutes and incubated at 37° C. for 4 hours. Samples were washed with PBS twice and an ADCC detection kit was added followed the protocol provided by manufacturer and incubated at room temperature for 30 minutes. The percentage of cell lysis in the plate was estimated by the reading of OD530/590. Each study was repeated three times. Data are presented as mean±SD.

Figure 11A:
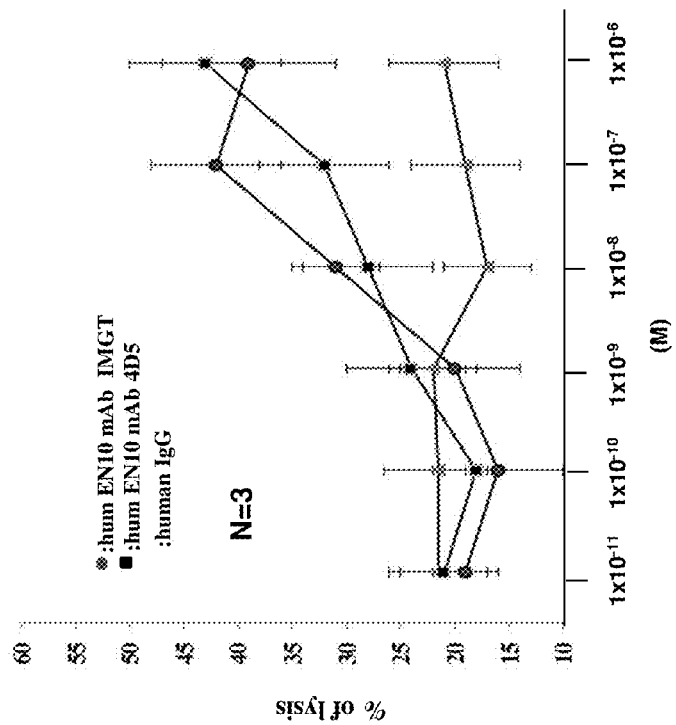
FIG. 11A and FIG. 11B depicts that the antibody-dependent cell-mediated cytotoxicity effects of humEN10 mAb 4D5 and humEN10 mAb IMGT antibodies. The administration of humanized antibodies and cell lysis effects of lung cancer cell line of CL1-5 were performed as described in Example 11. The data show that both humanized EN10 antibodies create new ADCC activities.
Figure 11B:
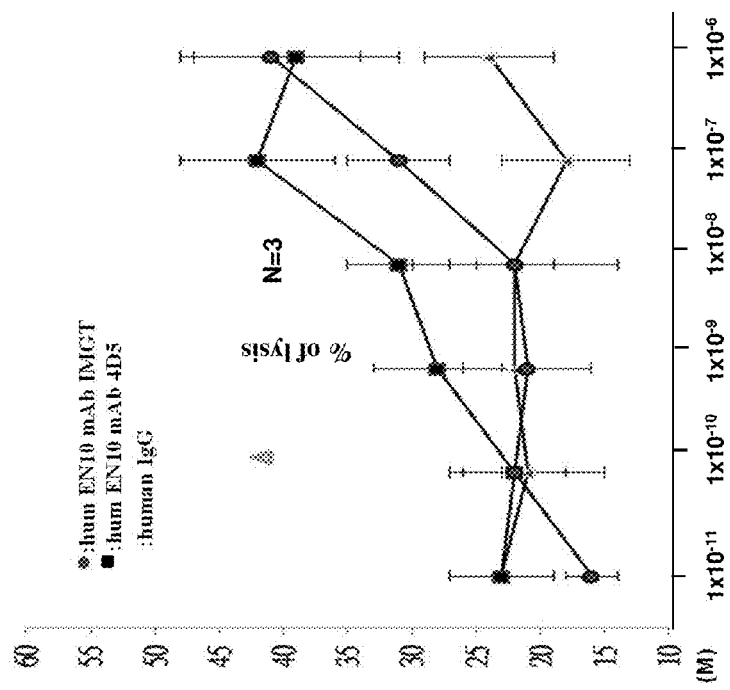

Results from these experiments are shown in FIGS. 11A and 11B. Cell lysis percentage shows no significant increase when cell were administrated with different concentration of control human IgG antibody in effector/Target ratio 40:1 and 1:15 studies. In effector/Target ratio 40:1 study, Cells treated with 1×10$^{-9}$ M of hum EN10 mAb 4D5 antibody started to see significant lysis difference compared with cells treated with the same concentration of human IgG. Both hum EN10 mAb 4D5 and hum EN10 mAb IMGT antibodies showed the maximum lysis activity about 42% when cells were administrated with 10$^{-6}$M of antibodies. In low effector/Target ratio (15:1) study, both hum EN10 mAb 4D5 and hum EN10 mAb IMGT antibody groups started to the see significant lysis at 1×10$^{-8}$ M and reaches the maximum lysis at 10$^{-6}$M. The ADCC EC50 of hum EN10 mAb 4D5 and hum EN10 mAb IMGT antibodies are estimated about 8×10$^{-9}$M and 1×10$^{-8}$M, respectively. Both humanized EN10 antibodies have the ADCC activities. Our results suggest that in addition to anti-migration activity hum EN10 mAb 4D5 and hum EN10 mAb IMGT antibodies can provided the ADCC activity as an anti-cancer agent.

Example 12

The Inhibitory Effect of Humanized EN10 Antibodies on Tumor Growth

The humanized EN10 antibody has a good affinity with Kd about $2.311\pm0.003\times10^{-10}$ mol/L and a potential for the further development. To evaluate the therapeutic effects of humanized EN10 antibodies, a CL1-5 mouse xenograft model was performed. CL1-5F4 lung adenocarcinoma cells ($1\times10^6$ cells/mouse; 5 mice/group) were subcutaneously inoculated at day 0. The therapeutic procedure was performed 2 days after the tumor inoculation by administrating 10 mpk (mg/Kg) of an isotype control (CTL) hum EN10 mAb 4D5 or hum EN10 mAb IMGT antibody twice per week. The tumor volume and bodyweight of each mouse was measured weekly. Data are represented as mean±SD for individual groups.

Figure 12:
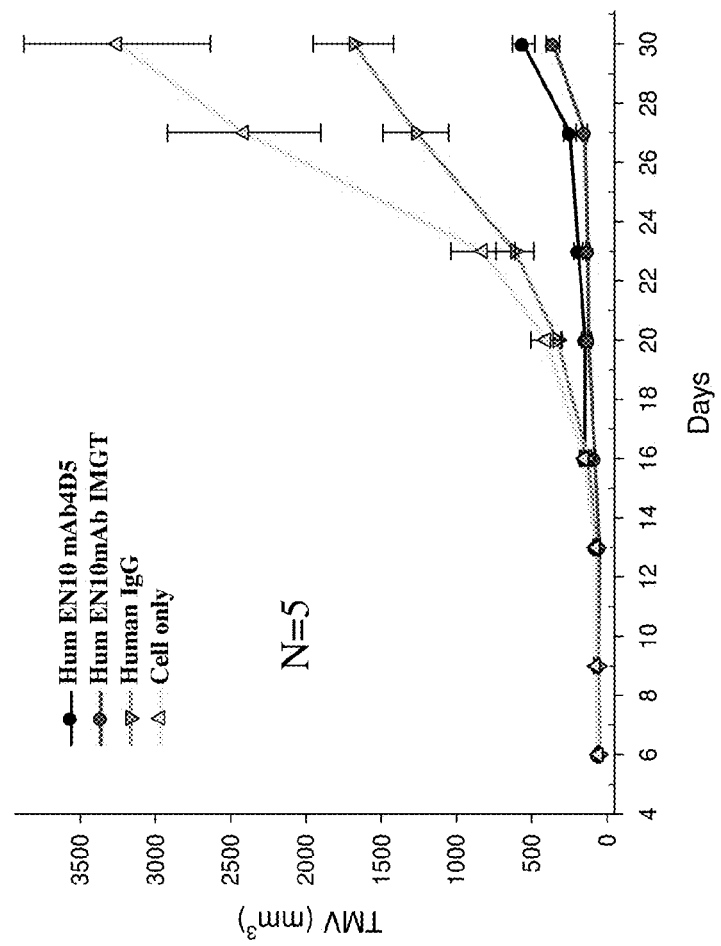
FIG. 12 shows inhibitory effects of humEN10 mAb 4D5 and humEN10 mAb IMGT antibodies. The administration of humEN10 mAb 4D5 and humEN10 mAb IMGT and the retardation of tumor growth by antibody treatment were performed as described in Example 12. The data show that the administration of both humanized EN10 mAbs twice per week has an efficacy in the CL1-5 xenograft mouse model.

The results are shown in FIG. 12. After 2 days, there are no significant tumor size differences among the control, hum EN10 mAb and hum EN10 mAb IMGT groups. After day 23, the tumor of mice in the control group starts to grow exponentially, and there is no significant tumor growth in the hum EN10 mAb 4D5 and hum EN10 mAb IMGT treatment mice. After day 30, the average tumor size of the control group mice is $1600\pm200$ mm$^3$ (N=5), and for mice treated with 10 mpk of hum EN10 mAb 4D5 and hum EN10 mAb IMGT, the average tumor sizes are 505±24 mm3 (N=5) and 330±11 mm3 (N=5), respectively. The average tumor sizes of both hum EN10 mAb 4D5 and hum EN10 mAb IMGT treatment groups are significantly smaller, as compared to that of the control group with a P value of 0.004 and 0.003, respectively. There are no significant tumor size difference tween hum EN10 mAb 4D5 and hum EN10 mAb IMGT treatment groups. This result indicates that hum ENID mAb 4D5 and hum EN10 mAb IMGT have the tumor growth inhibition activity on CL1-5 cells in the mouse xenograft model and EN10 mAb has a good efficacy as a reagent for cancer therapy.

Example 13

The CHO Cell Codon Optimization

From the examples above, we prospect ENO1 monoclonal antibody has potential to development as a therapeutic antibody.

To mass-produce the humanized therapeutic antibody in the CHO cell line, the codon optimization were performed. by using the GeneOptimizer® software tool. The variable region of hum EN10 mAb IMGT was subjected to obtain the optimized codons. The parameters include the codon quality distribution (the quality value of the most frequently used codon for the desired expression system) and GC content (optimizes codon so that GC content is within the desirable range). The codon optimized light chain variable region and heavy chain variable region for the CHO cell line show in FIG. 13A and FIG. 13B (SEQ ID NO: 14 and SEQ ID NO: 16), respectively.

The CHO cell codon optimized variable regions of light chain and heavy chains of hum EN10 mAb IMGT was directly generated by the nucleotide synthesis method, respectively. Then the variable regions of hum EN10 mAb IMGT and a human Herceptin$^R$ Fc antibody expression vector pCHO-ENO1, as shown in FIG. 13A, were introduced into host cells to prepare recombinant antibody-expressing cells. As the host cells for expression, the CHOS cells (Life-Technology Inc.) were used. The vector was introduced into the host cells by lipofectamine 2000 in accordance with the attached instruction manual (manufactured by Invitrogen.) About 2.5 microgram of the antibody expression vector was linearized by restriction enzymes, the gene was introduced into $4\times10^6$ cells, and cells were inoculated to a 6-well culture plate. For low concentration selection, resulting cell pools were grown in the selection medium containing 10 microgram/ml of puromycin and 100 nano molar of methotrexate or 20 microgram/ml of puromycin and 200 nano molar of methotrexate. To do the further selection, the other stage of high concentration selection was performed. The primary selection pools were further grown in the medium containing 30 microgram/ml of puromycin and 500 nano molar of methotrexate or in the medium containing 50 microgram/ml of puromycin and 1000 nano molar of methotrexate. To generate final antibody production cell line, 96,000 cells from the second stage pools were inoculated in semisolid medium and 768 high antibody expression cells were determined and picked by the fluorescence intensity performed in the ClonePix2 in accordance with the instruction manual protocol (manufactured by Molecular Device Inc.). The top 10 high lead cell lines were selected with parameters including growth rates, 5 day batch production rates and 14 day simple-fed batch production rates. After 60-generations of stability tests, the candidate production cell line was determined.

Figure 13B:
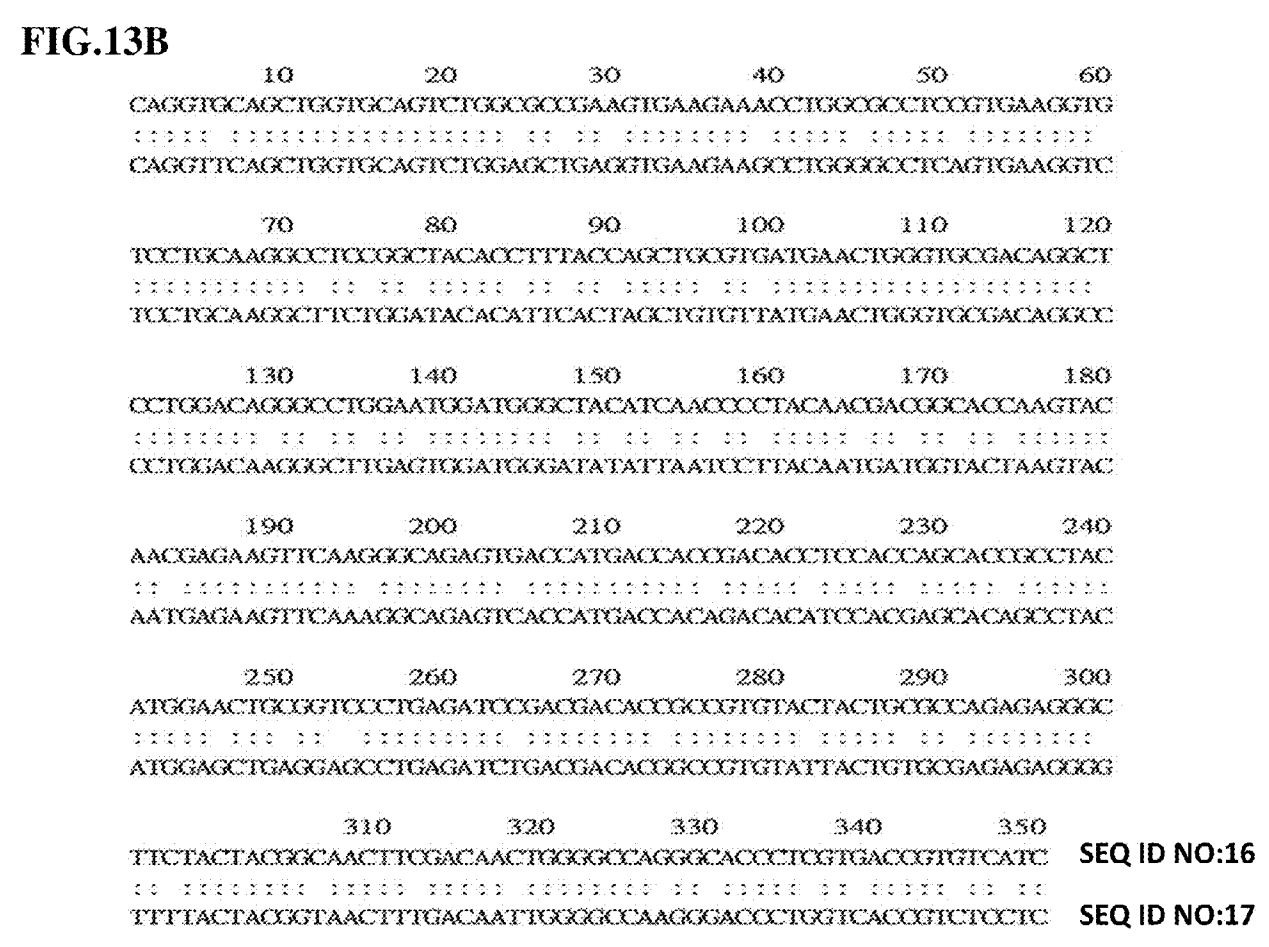
Figure 13C:
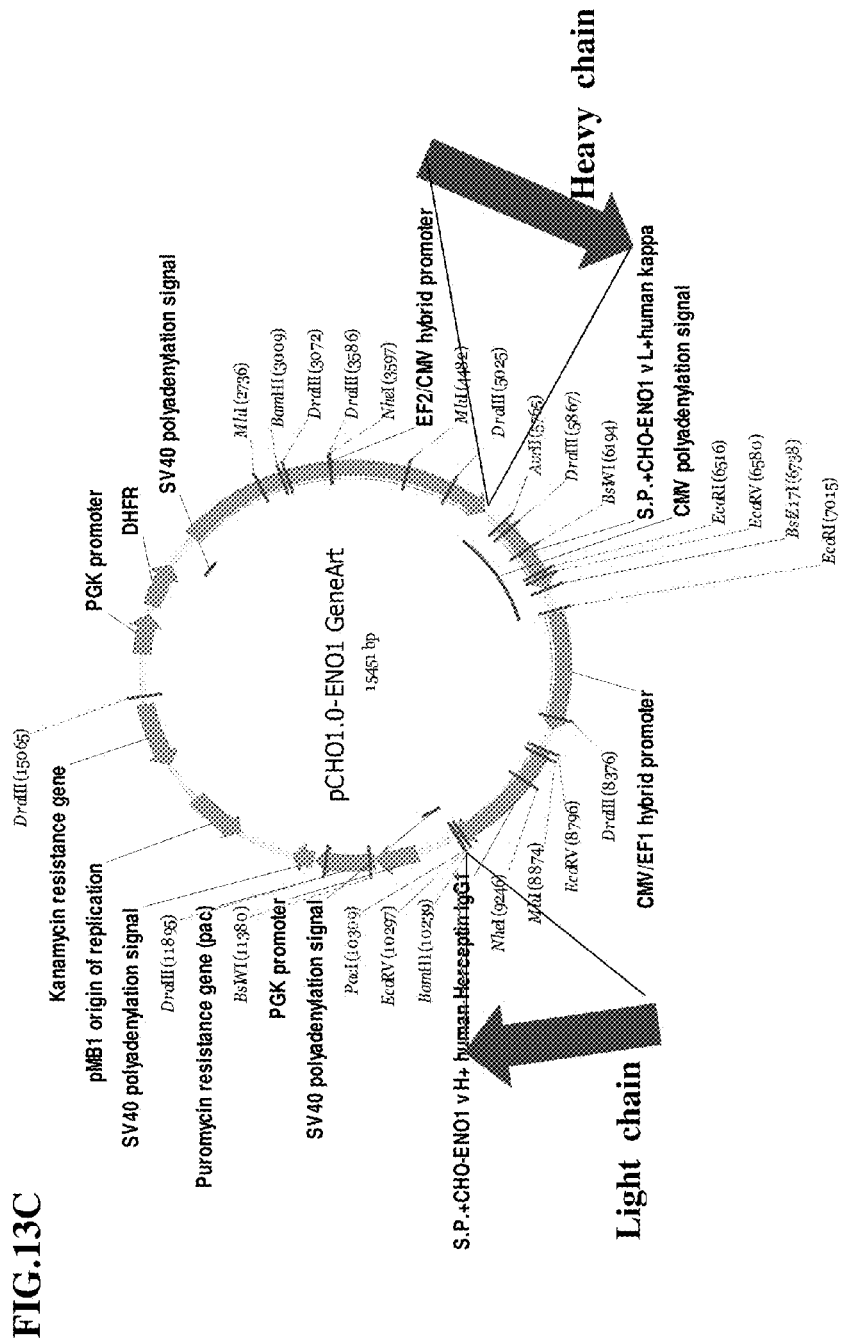
FIG. 13C shows the productivity of top 6 CHOS stable clones which expressed hum EN10 IMGT mAb antibody. Detail procedures were performed as described in Example 13. Our data shows that after the codon optimization and single colony selection, the production rates of these 6 top clones are close to 1 g/L/15 days.
Figure 13E:
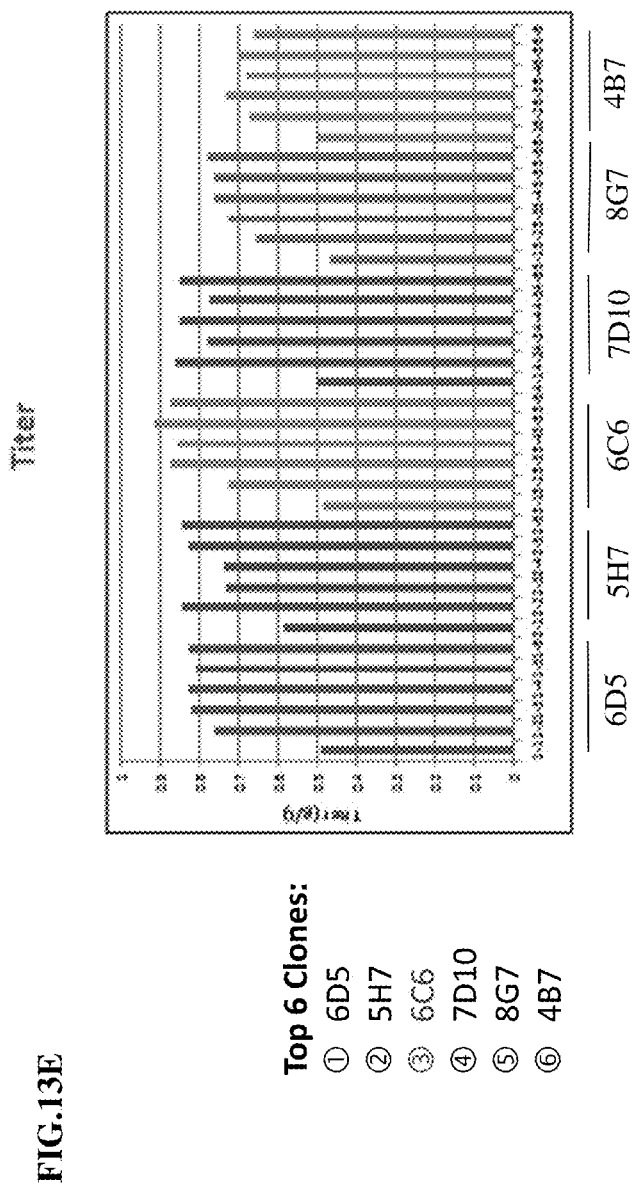
FIG. 13E shows the titers of the top 6 stable clones which expressed humEN10 mAb IMGT antibody. Detail procedures were performed as described in Example 13.
Figure 13F:
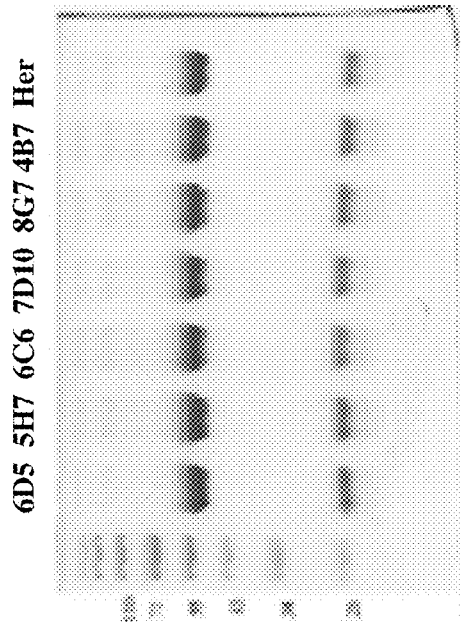
FIG. 13F shows the SDS PAGE of antibodies isolated from top 6 stable clones which expressed humEN10 mAb IMGT antibody. Detail procedures were performed as described in Example 13. Our data shows that all of these clones expresses intact hum EN10 mAb IMGT.

The results are shown the FIG. 13A. When the nucleic acid of the hum EN10 mAb IMGT which codons were optimized into the CHO cell expression system by the GeneOptimizer® software tool was aligned with that of human original, the homologies of variable light chain and variable heavy chain between two editions are 74.5% and 84%, respectively. This result indicates that the codon favor between human cells and CHO cells are different even the encoded antibody has the same protein sequence. When both editions of antibody genes were constructed to pCHO1.0 and transiently expressed in CHO cells, the antibody production rate of the CHO cell codon edition is about 3.1 time of that of human original (data not shown). Our result suggests that the codon optimization is very important for the high yield production of antibody. The cell pools of CHO optimized hum ENO10 mAb IMGT were further selected in the ForiCHO medium (Life Technology Inc.) and high antibody production cell lines were picked with a ClonePix2. When the production rates of top 15 clones on days 5 and 14 were analyzed, the results are shown in the FIG. 13B. The production rates ranges from 155 minigram/titer to 91.3 mg/liter on the day 5 and from 358.7 mg/titer to 247.5 mg/liter on the day 14. All of these clones have good viability and growth rate in the simple medium. These results suggest that all of clone may improve their antibody production capability after medium optimization. To further explore the antibody productivity of these clones, different combinations of glucose and feed medium studies were performed and the antibody productions rares were analyzed in the top 6 clones on the day 15. The result was shown in FIG. 13C. The maximum production rate of the top 6 clones ranges from 0.7 gram per liter to 0.81 gram per liter after 15 days incubation. All clones have good stability after 60-generation analysis and produce intact antibody when the antibodies were analyzed by SDS PAGE (FIG. 13D). Our study suggests that these clones have good potential as ENO1 therapeutic antibody production cell lines.

In sum, like antibody EN10 mAb, humanized EN10 mAb 4D5 and humanized EN10 mAb IMGT use their ENO1 plasminogen receptor antagonist activities to inhibit the plasminogen activation, thereby inducing down regulation of protease activity on the cell surface, which in turn results in the inhibition of dissociation of cancer cells from extracellular matrix. As a result, antibodies against ENO1 can inhibit the invasion capability of cancer cells. These data indicate that ENO1 antibodies (e.g., EN10 mAb) have favorable affinity, efficacy and potential as a therapeutic antibody for the treatment of cancers.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A humanized antibody, or a binding fragment thereof, wherein the humanized antibody binds human ENO1, wherein the antibody comprises a light chain variable region (VL) domain comprising a CDR1 having the amino acid sequence LCDR1 (RASENIYSYLT; SEQ ID NO: 6) and a CDR2 having the amino acid sequence LCDR2 (NAKTLPE; SEQ ID NO: 7) and a CDR3 having the amino acid sequence LCDR3 (QHHYGTPYT; SEQ ID NO: 8) and an antibody heavy chain variable region (VH) domain comprising a CDR1 having the amino acid sequence HCDR1 (GYTFTSCVMN; SEQ ID NO: 3), a CDR2 having the amino acid sequence HCDR2 (YINPYNDGTKYNEKFKG; SEQ ID NO: 4) and a CDR3 having the amino acid sequence HCDR3 (EGFYYGNFDN; SEQ ID NO: 5), wherein framework regions in the light chain variable region (VL) domain and the heavy chain variable region (VH) domain comprise amino acid sequences from a human immunoglobulin.

2. The antibody, or a binding fragment thereof, according to claim 1, wherein the VL domain comprises amino acid residues 1-110 of SEQ ID NO: 9.

3. The antibody, or a binding fragment thereof, according to claim 1, wherein the VH domain comprises amino acid residues 1-120 of SEQ ID NO: 10 or 11.

4. The antibody, or a binding fragment thereof, according to claim 2, wherein the VH domain comprises amino acid residues 1-120 of SEQ ID NO: 10 or 11.

5. The antibody, or a binding fragment thereof, according to claim 1, wherein the antibody has a constant region of an IgG1 type, and wherein the binding fragment thereof is an Fab fragment, an F(ab')$_2$ fragment, or an scFv fragment.

6. The antibody, or a binding fragment thereof, according to claim 2, wherein the antibody has a constant region of an IgG1 type, and wherein the binding fragment thereof is an Fab fragment, an F(ab')$_2$ fragment, or an scFv fragment.

7. The antibody, or a binding fragment thereof, according to claim 3, wherein the antibody has a constant region of an IgG1 type, and wherein the binding fragment thereof is an Fab fragment, an F(ab')$_2$ fragment, or an scFv fragment.

8. The antibody, or a binding fragment thereof, according to claim 4, wherein the antibody has a constant region of an IgG1 type, and wherein the binding fragment thereof is an Fab fragment, an F(ab')$_2$ fragment, or an scFv fragment.

9. The antibody, or a binding fragment thereof, according to claim 1, wherein the antibody, or the binding fragment thereof, can inhibit plasminogen receptor activity of ENO1.

10. The antibody, or a binding fragment thereof, according to claim 1, wherein the antibody, or the binding fragment thereof, can bind to human ENO1 with a dissociation constant ($K_d$) of 10 nM or lower.

11. The antibody, or a binding fragment thereof, according to claim 1, wherein the antibody is a monoclonal antibody.

12. A pharmaceutical composition for treating lung, breast, pancreas, liver, colorectal, or prostate cancer, the pharmaceutical composition comprising the antibody, or the binding fragment thereof, according to claim 1.

13. An expression vector comprising a polynucleotide encoding the antibody, or the binding fragment thereof, according to claim 1.

14. A cell comprising the expression vector of claim 9.

15. The cell according to claim 14, wherein the cell is a CHO cell.

* * * * *

```
                              SEQUENCE LISTING

<160> NUMBER OF SEQ ID NOS: 17

<210> SEQ ID NO 1
<211> LENGTH: 119
<212> TYPE: PRT
<213> ORGANISM: Mus musculus

<400> SEQUENCE: 1

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Cys
            20                  25                  30

Val Met Asn Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Glu Gly Phe Tyr Tyr Gly Asn Phe Asp Asn Trp Gly Gln Gly
            100                 105                 110

Thr Thr Leu Thr Val Ser Ser
        115

<210> SEQ ID NO 2
<211> LENGTH: 108
<212> TYPE: PRT
<213> ORGANISM: Mus muculus

<400> SEQUENCE: 2

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Thr Trp Tyr Gln Gln Lys Gln Gly Lys Ser Pro Gln Leu Leu Val
        35                  40                  45

Tyr Asn Ala Lys Thr Leu Pro Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Tyr Gly Thr Pro Tyr
                85                  90                  95

Thr Phe Gly Gly Gly Thr Lys Leu Glu Ile Thr Arg
            100                 105

<210> SEQ ID NO 3
<211> LENGTH: 10
<212> TYPE: PRT
<213> ORGANISM: Mus muculus
```

```
<400> SEQUENCE: 3

Gly Tyr Thr Phe Thr Ser Cys Val Met Asn
1               5                   10

<210> SEQ ID NO 4
<211> LENGTH: 17
<212> TYPE: PRT
<213> ORGANISM: Mus muculus

<400> SEQUENCE: 4

Tyr Ile Asn Pro Tyr Asn Asp Gly Thr Lys Tyr Asn Glu Lys Phe Lys
1               5                   10                  15

Gly

<210> SEQ ID NO 5
<211> LENGTH: 10
<212> TYPE: PRT
<213> ORGANISM: Mus muculus

<400> SEQUENCE: 5

Glu Gly Phe Tyr Tyr Gly Asn Phe Asp Asn
1               5                   10

<210> SEQ ID NO 6
<211> LENGTH: 11
<212> TYPE: PRT
<213> ORGANISM: Mus muculus

<400> SEQUENCE: 6

Arg Ala Ser Glu Asn Ile Tyr Ser Tyr Leu Thr
1               5                   10

<210> SEQ ID NO 7
<211> LENGTH: 7
<212> TYPE: PRT
<213> ORGANISM: Mus muculus

<400> SEQUENCE: 7

Asn Ala Lys Thr Leu Pro Glu
1               5

<210> SEQ ID NO 8
<211> LENGTH: 9
<212> TYPE: PRT
<213> ORGANISM: Mus muculus

<400> SEQUENCE: 8

Gln His His Tyr Gly Thr Pro Tyr Thr
1               5

<210> SEQ ID NO 9
<211> LENGTH: 108
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Thr Trp Tyr Gln Gln Lys Pro Gly Lys Ala Pro Lys Leu Leu Ile
        35                  40                  45
```

```
Tyr Asn Ala Lys Thr Leu Pro Glu Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His His Tyr Gly Thr Pro Tyr
                 85                  90                  95

Thr Phe Gly Gln Gly Thr Lys Leu Glu Ile Lys Arg
            100                 105
```

<210> SEQ ID NO 10
<211> LENGTH: 119
<212> TYPE: PRT
<213> ORGANISM: Homo sapiens

<400> SEQUENCE: 10

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Ser Cys
             20                  25                  30

Val Met Asn Trp Val Arg Gln Ala Pro Gly Lys Gly Leu Glu Trp Val
         35                  40                  45

Ala Tyr Ile Asn Pro Tyr Asn Asp Gly Thr Lys Tyr Asn Glu Lys Phe
     50                  55                  60

Lys Gly Arg Phe Thr Ile Ser Arg Asp Asp Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Phe Tyr Tyr Gly Asn Phe Asp Asn Trp Gly Gln Gly
            100                 105                 110

Thr Leu Val Thr Val Ser Ser
            115
```

<210> SEQ ID NO 11
<211> LENGTH: 119
<212> TYPE: PRT
<213> ORGANISM: Homo sapiens

<400> SEQUENCE: 11

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Cys
             20                  25                  30

Val Met Asn Trp Val Arg Gln Ala Pro Gly Gln Gly Leu Glu Trp Met
         35                  40                  45

Gly Tyr Ile Asn Pro Tyr Asn Asp Gly Thr Lys Tyr Asn Glu Lys Phe
     50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Glu Gly Phe Tyr Tyr Gly Asn Phe Asp Asn Trp Gly Gln Gly
            100                 105                 110

Thr Leu Val Thr Val Ser Ser
            115
```

```
<210> SEQ ID NO 12
<211> LENGTH: 18
<212> TYPE: DNA
<213> ORGANISM: Artificial Sequence
<220> FEATURE:
<223> OTHER INFORMATION: Synthetic

<400> SEQUENCE: 12
gtaaacaacg acggcgag                                                       18

<210> SEQ ID NO 13
<211> LENGTH: 17
<212> TYPE: DNA
<213> ORGANISM: Artificial Sequence
<220> FEATURE:
<223> OTHER INFORMATION: Synthetic

<400> SEQUENCE: 13
caggaaacag ctatgac                                                        17

<210> SEQ ID NO 14
<211> LENGTH: 300
<212> TYPE: DNA
<213> ORGANISM: Artificial Sequence
<220> FEATURE:
<223> OTHER INFORMATION: Synthetic

<400> SEQUENCE: 14
gacatccaga tgacccagtc cccctccagc ctgtctgcct ctgtgggcga cagagtgacc          60
atcacctgtc gggcctccga gaacatctac tcctacctga cctggtatca gcagaagccc         120
ggcaaggccc ccaagctgct gatctacaac gccaagaccc tgcccgaggg cgtgccctct         180
agattctccg gctctggctc tggcaccgac tttaccctga ccatcagctc cctgcagccc         240
gaggacttcg ccacctacta ctgccagcac cactacggca cccctacac ctttggccag          300

<210> SEQ ID NO 15
<211> LENGTH: 323
<212> TYPE: DNA
<213> ORGANISM: Homo sapiens

<400> SEQUENCE: 15
gatatccaga tgacccagtc ccccagctcc ctgtccgcct ctgtgggcga tagggtcacc          60
atcacctgcc gagcaagtga gaatatttac agttatttaa catggtatca acagaaacca         120
ggaaaagctc cgaaactact gatttacaat gcaaaaacct taccagaagg agtcccttct         180
cgcttctctg gttccggctc tgggacggat ttcactctga ccatcagcag tctgcagccg         240
gaagacttcg caacttatta cagtcaacat cattatggta ctccgtacac gttcggacag         300
ggtaccaagg tggagatcaa acg                                                 323

<210> SEQ ID NO 16
<211> LENGTH: 356
<212> TYPE: DNA
<213> ORGANISM: Artificial Sequence
<220> FEATURE:
<223> OTHER INFORMATION: Synthetic

<400> SEQUENCE: 16
caggtgcagc tggtgcagtc tggcgccgaa gtgaagaaac ctggcgcctc cgtgaaggtg          60
tcctgcaagg cctccggcta cacctttacc agctgcgtga tgaactgggt gcgacaggct         120
cctggacagg gcctggaatg gatgggctac atcaacccct acaacgacgg caccaagtac         180
```

```
aacgagaagt tcaagggcag agtgaccatg accaccgaca cctccaccag caccgcctac      240
atggaactgc ggtccctgag atccgacgac accgccgtgt actactgcgc cagagagggc      300
ttctactacg gcaacttcga caactggggc cagggcaccc tcgtgaccgt gtcatc          356

<210> SEQ ID NO 17
<211> LENGTH: 356
<212> TYPE: DNA
<213> ORGANISM: Homo sapiens

<400> SEQUENCE: 17
caggttcagc tggtgcagtc tggagctgag gtgaagaagc ctggggcctc agtgaaggtc       60
tcctgcaagg cttctggata cacattcact agctgtgtta tgaactgggt gcgacaggcc      120
cctggacaag ggcttgagtg gatgggatat attaatcctt acaatgatgg tactaagtac      180
aatgagaagt tcaaaggcag agtcaccatg accacagaca catccacgag cacagcctac      240
atggagctga ggagcctgag atctgacgac acggccgtgt attactgtgc gagagagggg      300
ttttactacg gtaactttga caattggggc caagggaccc tggtcaccgt ctcctc          356
```